(12) United States Patent
Uchida

(10) Patent No.: US 8,292,431 B2
(45) Date of Patent: Oct. 23, 2012

(54) MEDICAL IMAGING APPARATUS

(75) Inventor: Hiroki Uchida, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 27 days.

(21) Appl. No.: 12/490,316

(22) Filed: Jun. 24, 2009

(65) Prior Publication Data

US 2009/0323021 A1 Dec. 31, 2009

(30) Foreign Application Priority Data

Jun. 26, 2008 (JP) .................................. 2008-167062

(51) Int. Cl.
  *A61B 3/14* (2006.01)
  *A61B 3/00* (2006.01)
(52) U.S. Cl. ........................................ 351/206; 351/246
(58) Field of Classification Search .................... 351/206
  See application file for complete search history.

(56) References Cited

U.S. PATENT DOCUMENTS

| | | | | |
|---|---|---|---|---|
| 7,677,729 B2 * | 3/2010 | Vilser et al. .................... | 351/206 |
| 2002/0049733 A1 * | 4/2002 | Orlick .............................. | 707/1 |
| 2004/0095554 A1 * | 5/2004 | Ono ............................... | 351/206 |
| 2006/0280489 A1 | 12/2006 | Mizuochi | |
| 2008/0218600 A1 * | 9/2008 | Grosso et al. .............. | 348/231.6 |
| 2009/0323022 A1 * | 12/2009 | Uchida .......................... | 351/206 |
| 2010/0129849 A1 * | 5/2010 | Kiyota ............................ | 435/29 |

FOREIGN PATENT DOCUMENTS

| | | |
|---|---|---|
| JP | 2004-180705 A | 7/2004 |
| JP | 2005-196535 A | 7/2005 |
| JP | 2006-075512 A | 3/2006 |
| JP | 2006-115925 A | 5/2006 |
| JP | 2006-345955 A | 12/2006 |
| WO | WO 2009/001759 | * 12/2008 |

* cited by examiner

*Primary Examiner* — Jordan Schwartz
(74) *Attorney, Agent, or Firm* — Canon U.S.A., Inc. IP Division

(57) ABSTRACT

A medical imaging apparatus capable of concurrently performing a plurality of imaging operations including an imaging sequence setting unit configured to set a sequence for each of the plurality of imaging operations, an overlapping determination unit configured to determine temporal overlapping between an imaging sequence of an imaging operation that is currently performed and an imaging sequence for an imaging operation that is to be started, and an imaging sequence adjustment unit configured to adjust, based on a result of determination made by the overlapping determination unit, the imaging sequence for the imaging operation that is to be started.

28 Claims, 20 Drawing Sheets

FIG. 5

| | IMAGING MODE | | AGE THRESHOLD | AGE COEFFICIENT |
|---|---|---|---|---|
| | Color | Fluo | | |
| PREPARATION TIME BEFORE IMAGING | 0'30" | 1'00" | 50 | ×10 |
| PREPARATION TIME AFTER IMAGING | 0'10" | 0'30" | 50 | ×10 |

FIG. 8

EXAMINATION APPOINTMENT

PATIENT ID: 0002
PATIENT NAME: SUZUKI HANAKO
AGE: 60

IMAGING SEQUENCE

| No. | IMAGING MODE | RIGHT/LEFT EYE | IMAGING TIMING | PREPRATION TIME BEFORE IMAGING | PREPRATION TIME AFTER IMAGING |
|---|---|---|---|---|---|
| 1 | Fluo | RIGHT EYE | 0' 04" | 1' 10" | 0' 40" |
| 2 | Fluo | RIGHT EYE | 0' 05" | 1' 10" | 0' 40" |
| 3 | Fluo | RIGHT EYE | 0' 10" | 1' 10" | 0' 40" |
| 4 | Color | RIGHT EYE | 0' 30" | 0' 40" | 0' 20" |
| 5 | Color | LEFT EYE | 0' 50" | 0' 40" | 0' 20" |
| 6 | Fluo | RIGHT EYE | 3' 00" | 1' 10" | 0' 40" |
|   |   |   |   |   |   |

ADD SEQUENCE     APPOINT

MEDICAL IMAGING APPARATUS

BACKGROUND OF THE INVENTION

1. Field of the Invention

The present invention relates to a medical imaging apparatus, such as a fundus camera to be used for a group examination, at an ophthalmologist's office, and the like.

2. Description of the Related Art

In these days, fundus imaging using a fundus camera has been widely used for screening in group examinations, and diagnosis for ophthalmological disease. In recent years, a method for recording a fundus image as digital data has been widely used. Imaged data is recorded in portable type recording media and hard disk drives built in personal computers (PCs).

In order to improve efficiency of fundus imaging, fundus cameras capable of concurrently performing a plurality of fundus imaging operations have become widely used. Particularly, when fluorescence imaging using a fluorescence agent is performed in an ophthalmologist's office, in many cases, when several minutes or several tens of minutes have passed after a large number of fundus images are taken at an initial stage at which intravenous injection of a fluorescence agent is performed, later stage imaging is performed.

Accordingly, a waiting time occurs while fluorescence imaging is performed on a subject. Thus, an operator may perform color imaging during the waiting time. Thereby, examination efficiency can be improved.

In a fundus camera discussed in, e.g., Japanese Patent Application Laid-Open No. 2006-345955, color imaging of a subject can be performed while fluorescence imaging of the same subject is performed. However, when fluorescence imaging and color imaging of a subject are concurrently performed, an operator may not recognize in which imaging mode the current imaging is performed.

Thus, in the fundus camera discussed in Japanese Patent Application Laid-Open No. 2006-345955, when a predetermined number of images of a subject are captured in color after the color imaging is once performed while the fluorescence imaging is performed, the current imaging mode is automatically returned to the fluorescence imaging mode. As a result, an operator can take images of a subject without confusion.

As described above, in recent years, with rapid digitalization of fundus cameras, requests for concurrently performing a plurality of fundus imaging operations have increased. Particularly, because a film exchange operation needed when a subject is changed is not necessary because of the digitalization of fundus cameras, requests for performing fundus imaging of another subject during the waiting time for a subject have increased.

However, when the fundus imaging is excessively inserted in the fundus imaging of the subject, the fundus imaging that is originally to be performed cannot be performed at a proper timing.

For example, when fluorescence imaging of a fundus of a subject's eye is performed in an ophthalmologist's office or the like, fundus imaging is performed by intravenously injecting a fluorescence agent into the subject. The intravenously injected fluorescence agent circulates in the subject's body. Eventually, the fluorescence agent reaches a fundus part of the subject's eye. An operator must take an image of the fundus part of the subject's eye at a timing when the fluorescence agent reaches a diseased portion of the fundus part of the subject's eye.

However, when imaging is concurrently performed on a plurality of subjects, a time for changing the subjects is necessary. Accordingly, a proper timing for capturing each image may be missed during the changing of the subjects.

Even when the changing of the subjects is smoothly performed, the proper timing of the fluorescence imaging may be missed if focus adjustment and alignment adjustment in the fundus camera take a lot of time.

Thus, when a plurality of subjects are concurrently imaged, a risk of missing the proper timing of imaging may occur in exchange for high examination efficiency. When an operator misses the proper timing of imaging of a subject, the operator must ask the subject for re-imaging.

This not only reduces the examination efficiency from a viewpoint of improving the efficiency but also imposes a large burden on a subject. In order to avoid the risk described above, operators must give up concurrent imaging of a plurality of subjects. As a result, the improvement of the examination efficiency may not be achieved.

SUMMARY OF THE INVENTION

The present invention is directed to a medical imaging apparatus capable of improving examination efficiency by increasing opportunities for concurrent fundus imaging.

According to an aspect of the present invention, a medical imaging apparatus capable of concurrently performing a plurality of imaging operations including an imaging sequence setting unit configured to set a sequence for each of the plurality of imaging operations, an overlapping determination unit configured to determine temporal overlapping between an imaging sequence of an imaging operation that is currently performed and an imaging sequence for an imaging operation that is to be started, and an imaging sequence adjustment unit configured to adjust, based on a result of determination made by the overlapping determination unit, the imaging sequence for the imaging operation that is to be started.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 5 illustrates a preparation time calculation table for calculating a pre-imaging preparation time and a post-imaging preparation time.

FIG. 8 illustrates an examination appointment screen after an imaging sequence is registered.

DETAILED DESCRIPTION OF THE EMBODIMENTS

Various exemplary embodiments, features, and aspects of the invention will be described in detail below with reference to the drawings.

Figure 1:
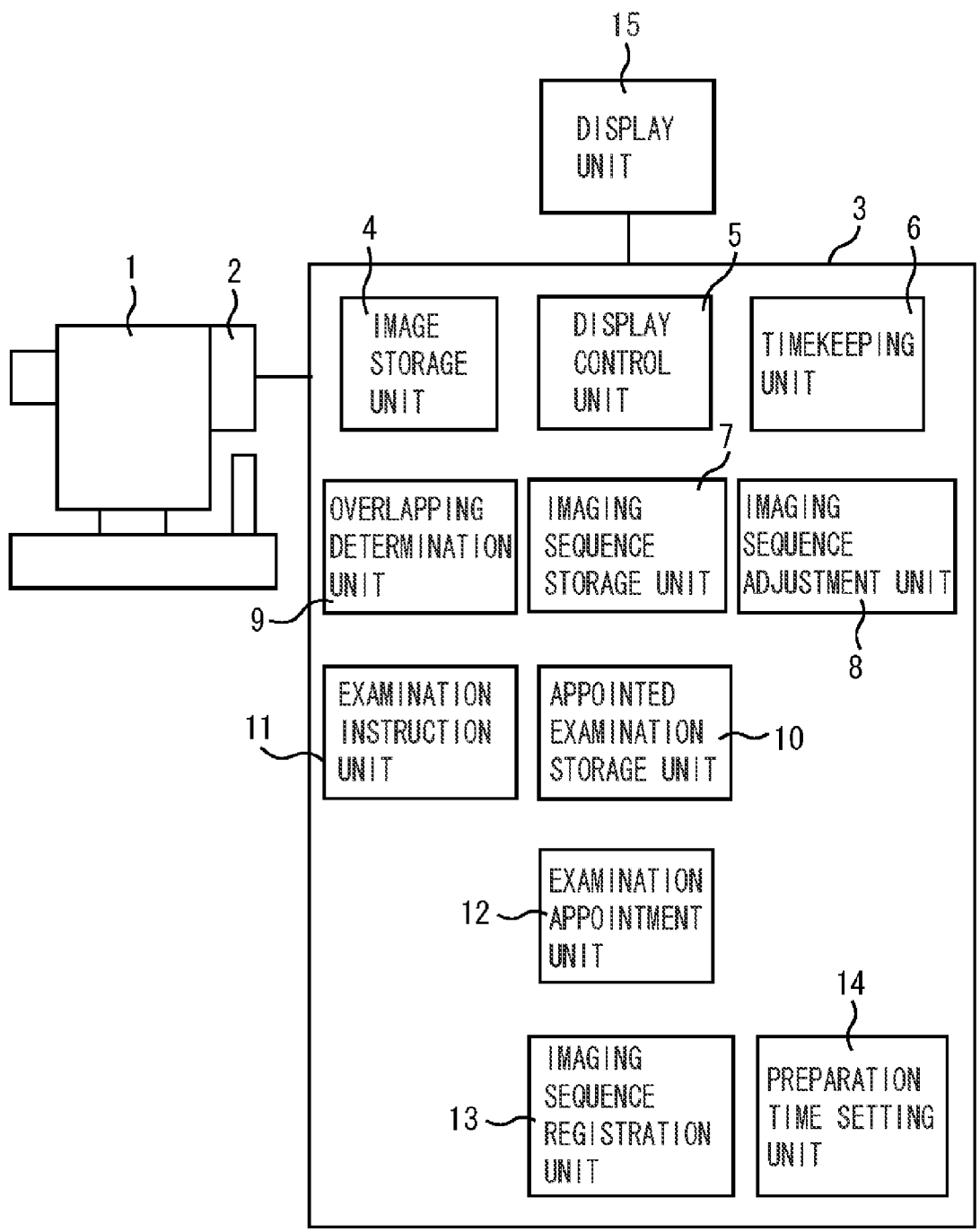
FIG. 1 illustrates a configuration of a fundus imaging apparatus.

FIG. 1 illustrates a configuration of a fundus imaging apparatus according to a first exemplary embodiment, which serves as a medical imaging apparatus.

A digital camera 2 including an image sensor that captures an image of a fundus of a subject's eye is attached to a fundus camera 1. An image captured by the digital camera 2 is output to an information processing apparatus 3.

The information processing apparatus 3 includes an image storage unit 4, a display control unit 5, a timer unit 6, an imaging sequence storage unit 7, an imaging sequence adjustment unit 8, an overlapping determination unit 9, an appointed examination storage unit 10, an examination instruction unit 11, an examination appointment unit 12, an imaging sequence registration unit 13, and a preparation time setting unit 14. A display unit 15 is connected to the information processing unit 3.

The display control unit 5 controls the display unit 15 to display information, based on images stored in the image storage unit 4, imaging sequences stored in the imaging sequence storage unit 7, and a time measured by the timer unit 6. The imaging sequence adjustment unit 8 adjusts an imaging sequence based on determination made by the overlapping determination unit 9. The examination instruction unit 11 can select, from among appointed examinations, an examination to be started.

Figure 2:
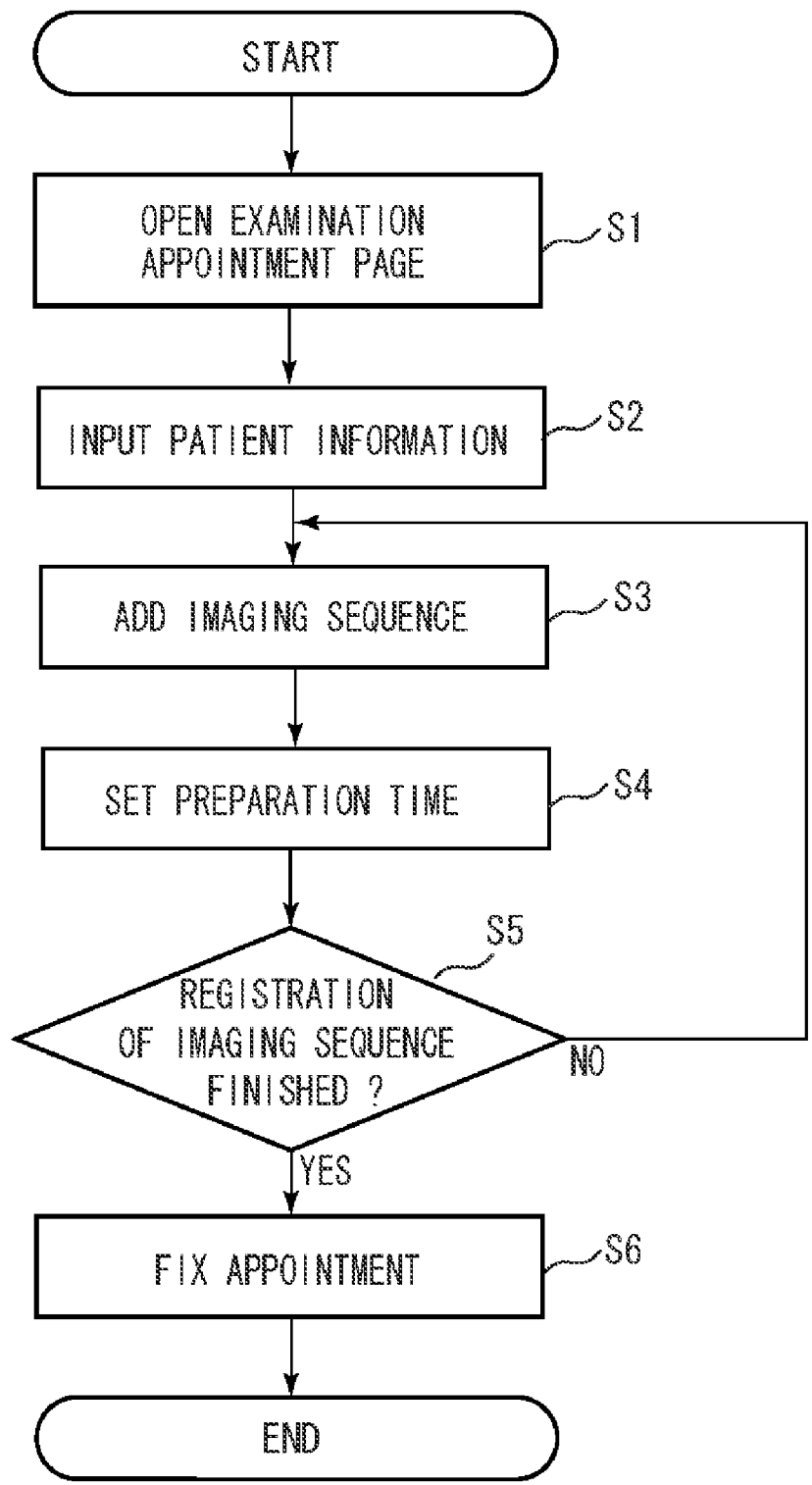
FIG. 2 is a flowchart illustrating a fundus imaging appointment procedure.

FIG. 2 is a flowchart illustrating a fundus imaging appointment procedure according to the present exemplary embodiment. First, before fundus imaging is performed, an operator operates the examination appointment unit 12. Thus, appointment of fundus imaging operations to be performed, and an imaging sequence for each of the fundus imaging operations are performed.

Figure 3:
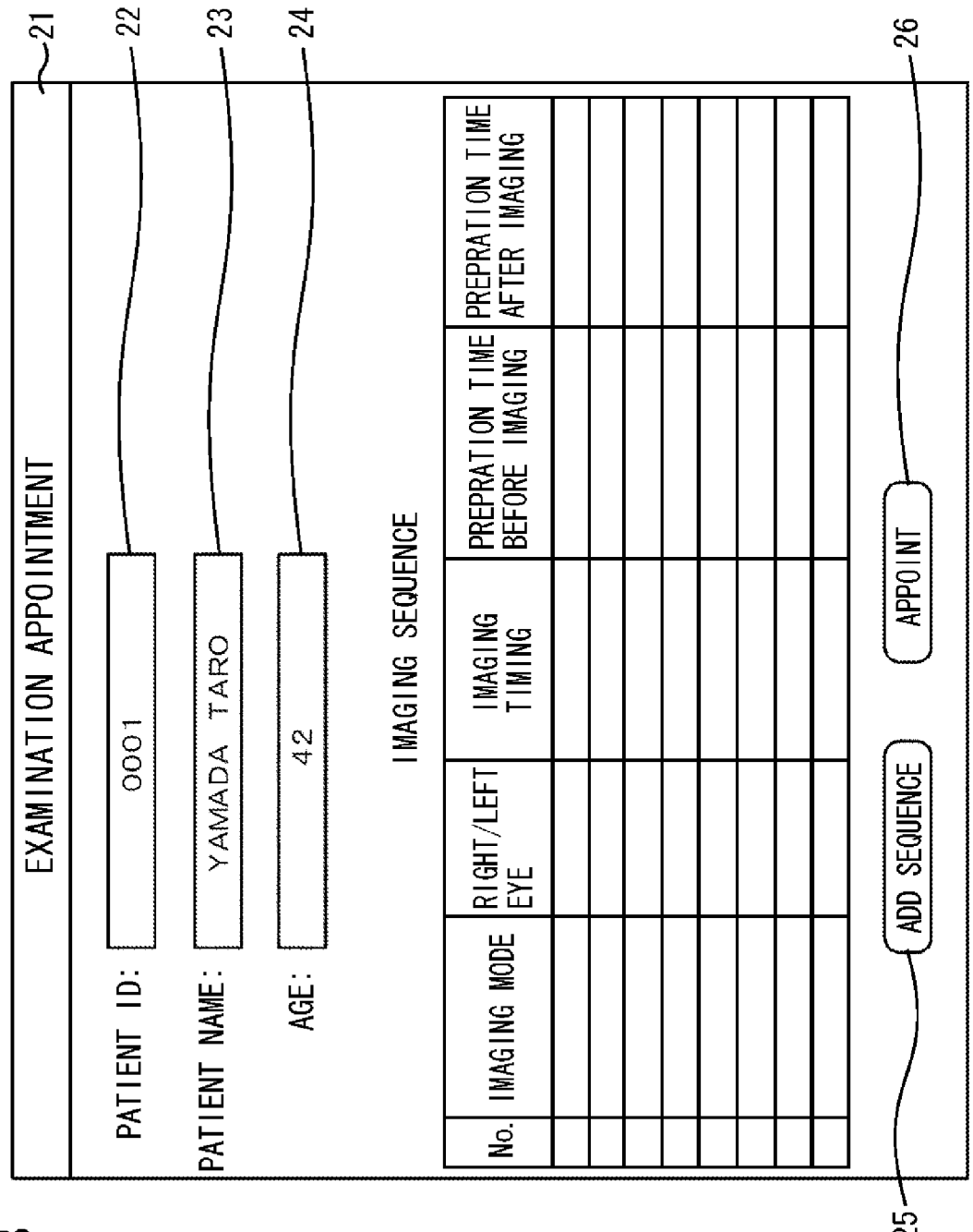
FIG. 3 illustrates an examination appointment screen before an imaging sequence is registered.

In the case of performing fluorescence imaging in an ophthalmologist's office, first, in step S1, when the display control unit 5 detects that the examination appointment unit 12 is operated, the display control unit 5 causes the display unit 15 to display an examination appointment screen 21 as illustrated in FIG. 3. The display control unit 5 displays a subject identification (ID) input field 22, a subject name input field 23, an age input field 24, a sequence addition button 25, and an appointment button 26 on the examination appointment screen 21. Then, control proceeds to step S2.

In step S2, when the examination appointment unit 12 detects an appointment operation performed by an operator, an accepted subject ID, an accepted subject name, and an accepted age are input to the subject ID input field 22, the subject name input field 23, and the age input field 24 as subject information.

Figure 4:
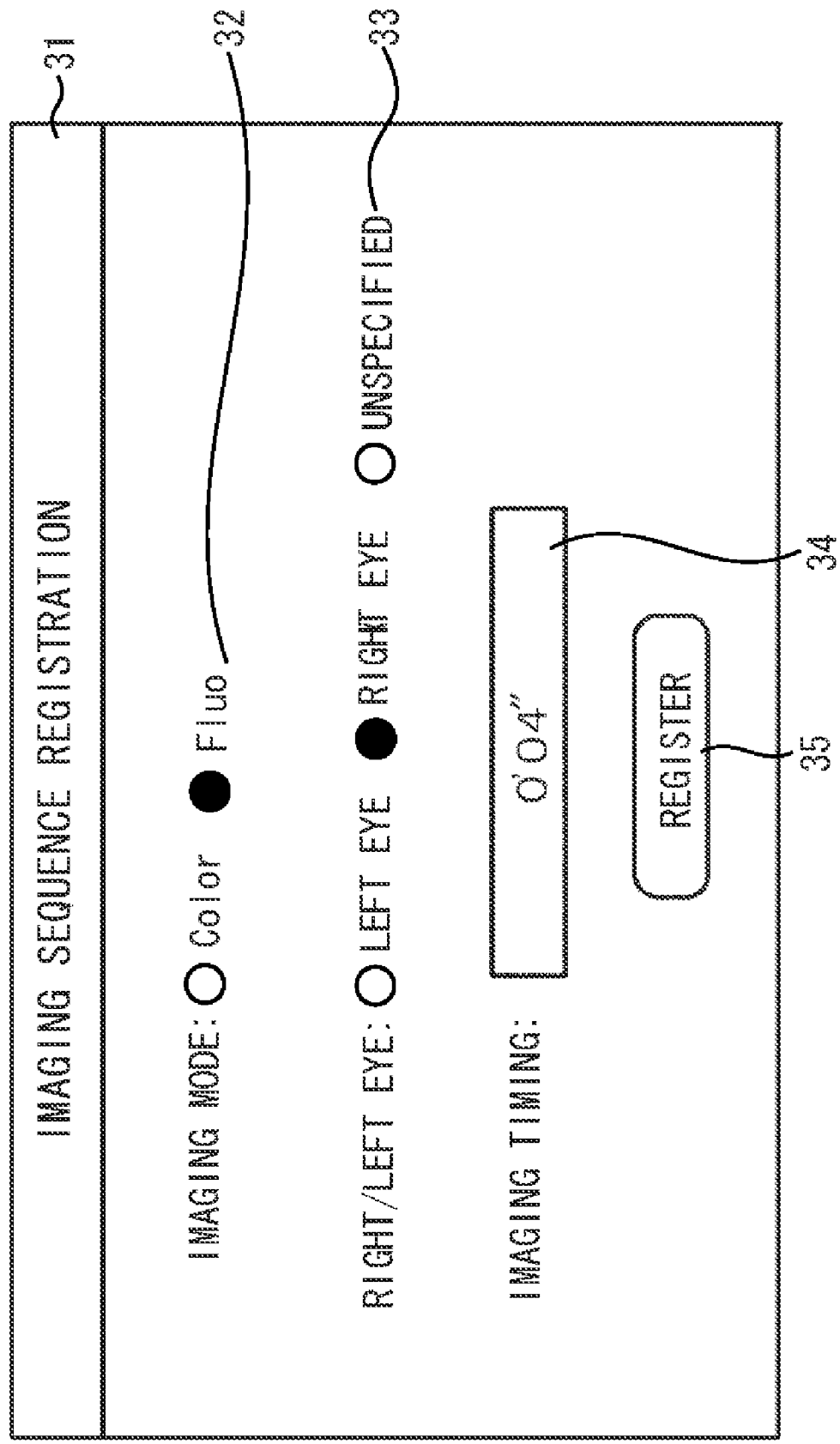
FIG. 4 illustrates an imaging sequence registration screen.

Next, in step S3, when the display control unit 5 detects that the sequence addition button 25 provided on the examination appointment screen 21 is selected, the display control unit 5 causes the display unit 15 to display a screen for registering an imaging sequence corresponding to a fundus imaging operation to be appointed on a display surface thereof, as illustrated in FIG. 4.

The imaging sequence registration unit 13 causes the imaging sequence storage unit 7 to store each registered item. The "imaging sequence" is defined as an imaging procedure including at least one of a imaging mode, information indicating which eye is a target to be captured, an imaging timing, and a permissible time for an imaging timing.

The imaging sequence registration screen 31 illustrated in FIG. 4 includes an imaging mode input field 32, an imaging condition input field 33 into which imaging conditions such as designation of an eye are input, and an imaging timing input field 34 into which a timing for imaging of each fundus is input. For example, when fluorescence imaging using a mydriatic type fundus camera is performed in an ophthalmologist's office, fluorescence imaging ("Fluo") is designated in the imaging mode input field 32 of the imaging sequence registration screen 31.

Next, when a right or left eye is designated in the imaging condition input field 33, when performing fluorescence imaging, in many cases a diseased part has already been specified. Thus, a specific eye (e.g., a "right eye") is designated on the imaging sequence registration screen 31 illustrated in FIG. 4.

Next, when the imaging timing is specified in the imaging timing input field 34, a lapse time since the intravenous injection of a fluorescence agent into a subject is an important factor for the fluorescence imaging. Thus, it is necessary to preliminarily specify a timing at which imaging should be performed. Therefore, the specified lapse time since the intravenous injection of a fluorescence agent into the subject is input to the imaging timing input field.

The imaging timing is not limited to the lapse time since the intravenous injection of a fluorescence agent. A lapse time since the imaging of a first image can be employed as the imaging timing.

Then, in step S4, when the selection of the registration button 35 on the imaging sequence registration screen 31 illustrated in FIG. 4 is detected, the preparation time setting unit 14 sets a preparation time according to the imaging sequence input in step S3.

The "preparation time" is defined as a time required to change subjects when a work of changing subjects is needed before or after the imaging of an image of the subject. For example, after the imaging of one subject is performed, a pre-imaging preparation time and a post-imaging preparation time are needed to perform imaging of another subject.

The post-imaging preparation time is defined as a time required to make a subject, whose image has been just captured, leave a seat. That is, in order to take an image of the next subject, it is necessary for an operator to cause the subject currently seated in front of the fundus camera 1 to move to another place where the subject does not hinder the imaging of the next subject. Accordingly, after a certain subject is imaged, a certain post-imaging preparation time should be provided.

The pre-imaging preparation time is defined as a time required to bring a subject other than the subject, whose image is currently captured, into a state to be imaged. Usually, a subject waiting for imaging of his fundus stands ready in a waiting room next to the examination room. Thus, it is necessary that after a subject, whose image has been taken until then, leaves a seat, the operator have the next subject move from the waiting room to the front of the fundus camera 1.

Then, the operator makes the next subject sit on the seat to perform alignment adjustment and focus adjustment of this subject's eye. When fluorescence imaging is started, it is necessary to intravenously inject a fluorescence agent into this subject and to operate the timer start button of the examination instruction unit 11.

Unless all of these operations are completed, imaging of a fundus of the next subject's eye cannot be started. Thus, generally, the pre-imaging preparation time may be longer than the post-imaging preparation time.

The preparation time setting unit 14 determines and sets the pre-imaging preparation time and the post-imaging preparation time described above. The preparation time setting unit 14 includes a storage portion configured to store a table illustrated in FIG. 5 and can determine a pre-imaging preparation time and a post-imaging preparation time for each imaging mode in fundus imaging.

Then, when the selection of the registration button 35 on the imaging sequence registration screen 31 illustrated in FIG. 4 is detected, the preparation time setting unit 14 refers to the table illustrated in FIG. 5 and acquires information on the pre-imaging preparation time and the post-imaging preparation time for the imaging mode specified in the imaging mode input field 32.

The acquired information on the pre-imaging preparation time and the post-imaging preparation time is stored in the imaging sequence storage unit 7 as a part of the imaging sequence, together with other input information. Thus, the imaging sequence concerning the fluorescence imaging of a first image is completed.

Although an example of setting a fixed preparation time for each imaging mode has been described above, sometimes, a fixed preparation time is insufficient for imaging. For example, when a subject is aged, a time necessary for the subject to leave the fundus camera 1 may be longer. In addition, a fixation state of a subject's eye may be deteriorated. Thus, the older the subject is, the longer the preparation time may become.

In order to address this problem, the fundus imaging apparatus according to the present exemplary embodiment is constructed to be able to adjust the preparation time according to the age of a subject. As is seen from the table illustrated in FIG. 5, the preparation time setting unit 14 stores an age threshold, and an age coefficient.

When the age of the subject is higher than a predetermined value, the pre-imaging preparation time and the post-imaging preparation time can be extended according to the age of the subject. A procedure for setting the preparation time is described in detail with reference to a flowchart described below.

In step S5, it is determined whether the registration of the imaging sequence is to be finished. If another imaging sequence is to be registered (NO in step S5), the operator may select the sequence addition button 25 provided on the examination appointment screen 21.

If the imaging sequence registration unit 13 detects the selection of the sequence addition button 25 (NO in step S5), the process returns to step S3. Then, an imaging sequence for a second image or later is registered. Such an operation of registering the imaging sequence is repeated, so that a series of imaging sequences is added. Thus, as is indicated by the examination appointment screen 21 illustrated in FIG. 6, the registered imaging sequences are displayed in the ascending order of the imaging timing.

In step S5, if it is determined that the operation of registering the imaging sequences is finished (YES in step S5), the process proceeds to step S6.

In step S6, if the control unit detects the selection of the appointment button 26 on the examination appointment screen 21, the examination appointment unit 12 definitely determines the appointment. Then, the input subject information is associated with the imaging sequence. The subject information is stored in the appointed examination storage unit 10.

Figure 7:
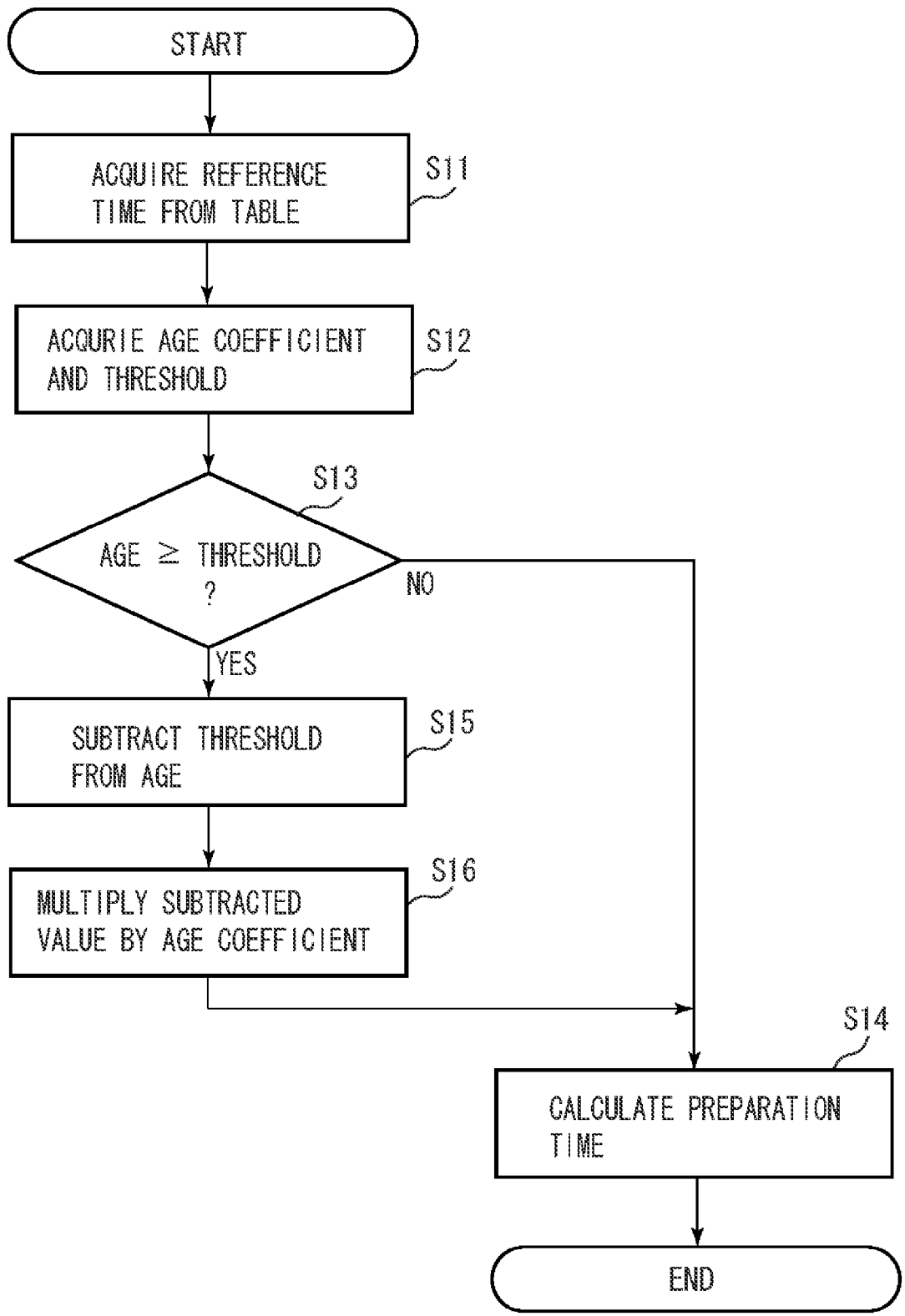
FIG. 7 is a flowchart illustrating a preparation time calculation process.

FIG. 7 is a flowchart illustrating a preparation time adjustment process for adjusting a preparation time, which is performed in step S4 according to the age of a subject.

In step S11, the preparation time setting unit 14 acquires a pre-imaging preparation time and a post-imaging preparation time, according to an imaging mode registered in the imaging sequence, from the preparation time table illustrated in FIG. 5. Then, in step S12, the preparation time setting unit 14 acquires an age threshold, and an age coefficient.

Next, in step S13, the preparation time setting unit 14 determines whether the age of the subject is equal to or higher than the age threshold. If the age of the subject is less than the threshold (NO in step S13), the processing proceeds to step S14. In step S14, the preparation time setting unit 14 calculates a value for each of the pre-imaging preparation time and the post-imaging preparation time and employs them as they are.

On the other hand, in step S13, if the age of the subject is equal to or higher than the threshold (YES in step S13), the process proceeds to step S15. In step S15, the preparation time setting unit 14 calculates a value by subtracting the age threshold from the age of the subject.

Subsequently, in step S16, the preparation time setting unit 14 calculates a definitive preparation time correction coefficient by multiplying the value, which is obtained in step S15 by the subtraction, by the age coefficient. Then, in step S14, the preparation time setting unit 14 multiplies each of the acquired pre-imaging preparation time and the acquired post-imaging preparation time by the preparation time correction coefficient obtained in step S16. Thus, the preparation time setting unit 14 calculates values of the pre-imaging preparation time and the post-imaging preparation time, taking the age of the subject into account.

As described above, the fundus imaging apparatus according to the present exemplary embodiment can extend the pre-imaging preparation time and the post-imaging preparation according to the age of a subject. Accordingly, an enough time for interchanging subjects can be secured.

According to the present exemplary embodiment, the pre-imaging preparation time and the post-imaging preparation are calculated using the preparation time table, i.e., the fixed age threshold, and the fixed age coefficient. However, a method for the calculation, and the age coefficient can arbitrarily be set. In addition, the preparation time setting unit 14 can be constructed to adjust the preparation time according to the level of skill of an operator. Alternatively, the preparation time setting unit 14 can be constructed so that each preparation time can be specified directly and arbitrarily.

Figure 6:
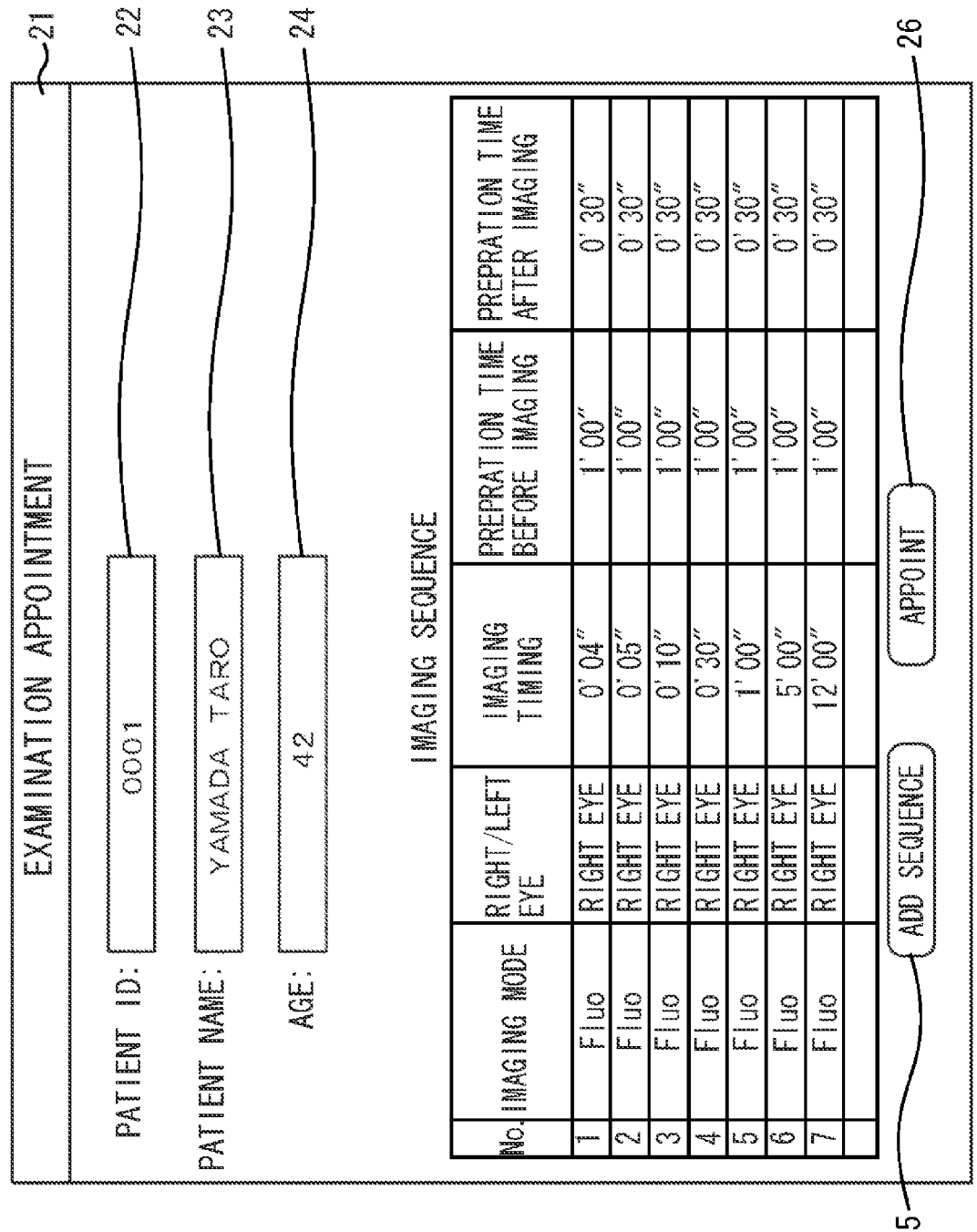
FIG. 6 illustrates an examination appointment screen after an imaging sequence is registered.

FIG. 8 illustrates the examination appointment screen 21 for another subject different from the subject illustrated in the examination appointment screen 21 illustrated in FIG. 6. On the examination appointment screen 21 illustrated in FIG. 8, information about the subject is input to the subject ID input field 22, the subject name input field 23, and the age input field 24, similarly to those of the first subject.

The registration of the imaging sequences is performed, similarly to that of the first subject. However, the imaging sequences different from those of the subject are set. This is because of the facts that disease conditions vary depending on the subjects, and that fundus imaging methods for them vary depending on the subjects.

Imaging sequences for the subject in FIG. 8 are registered in the corresponding examination appointment screen 21 so as to perform fundus imaging according to combinations of the fluorescence imaging mode ("Fluo") and the color imaging mode ("Color").

The subject illustrated in FIG. 8 is older than the first subject in FIG. 6. Thus, even in the same imaging mode, the preparation time for the subject is set to be longer than the first subject in FIG. 6. When the selection of the appointment button 26 is detected after the imaging sequence is registered, the appointment information of the second subject is also stored in the appointed examination storage unit 10.

When an appointed examination is performed, the operator make the subject, whose image is taken next, move in front of the fundus camera 1 before fundus imaging is performed. First, a subject, whose examination has been appointed and has ID "0001", is selected on the examination appointment screen 21 illustrated in FIG. 6.

Figure 9:
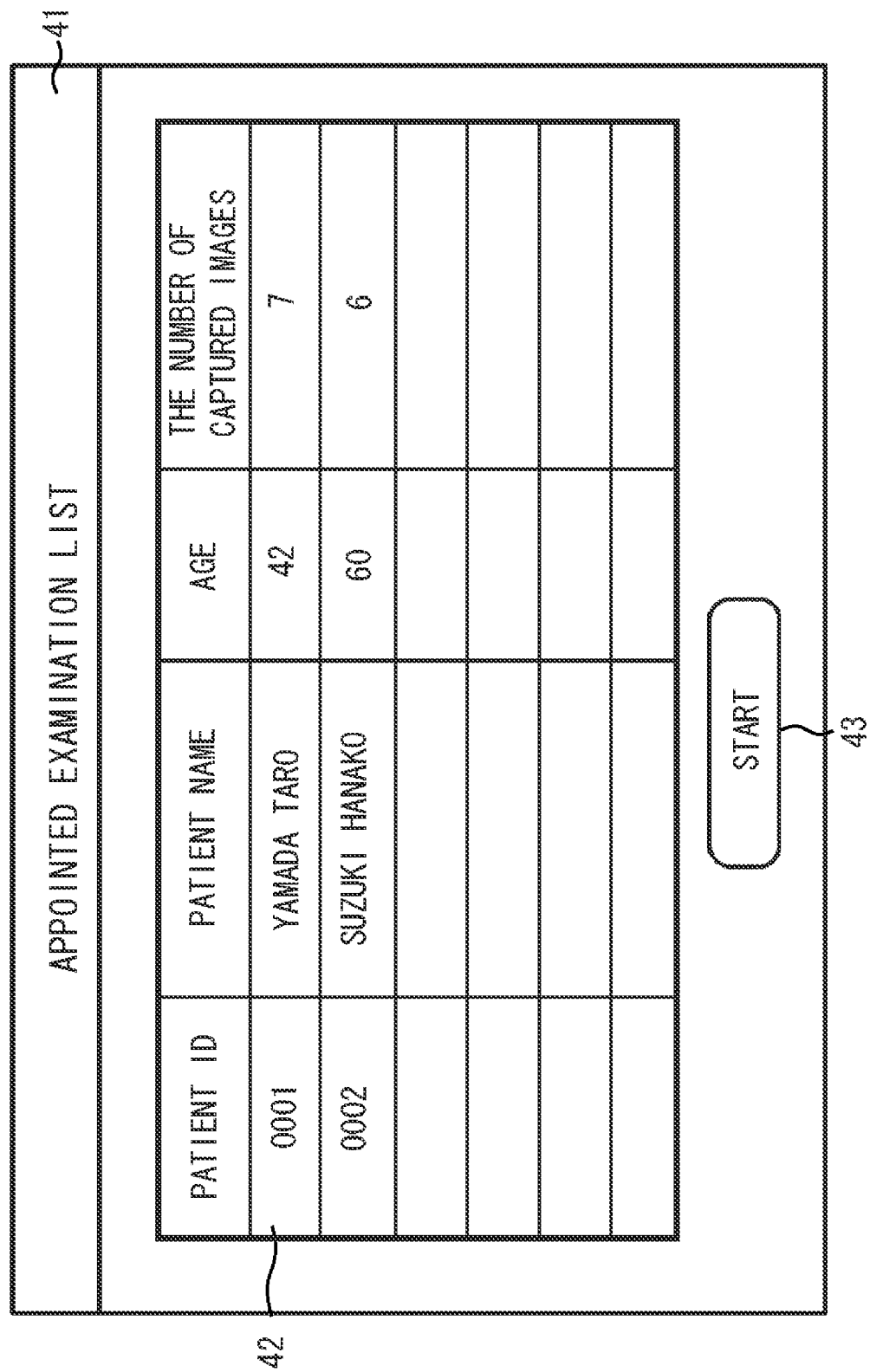
FIG. 9 illustrates an appointed examination list screen.

The operator operates the examination instruction unit 11 to cause the display unit 15 to display an appointed examination list screen 41 illustrated in FIG. 9. On the appointed examination list screen 41, every line of the appointed examination list shows information about each subject 42, the examination for which has been appointed via the examination appointment unit 12.

The operator chooses one of the subjects 42, whose imaging starts next, from the appointed examination list and selects the examination start button 43 to start fundus imaging.

Figure 10:
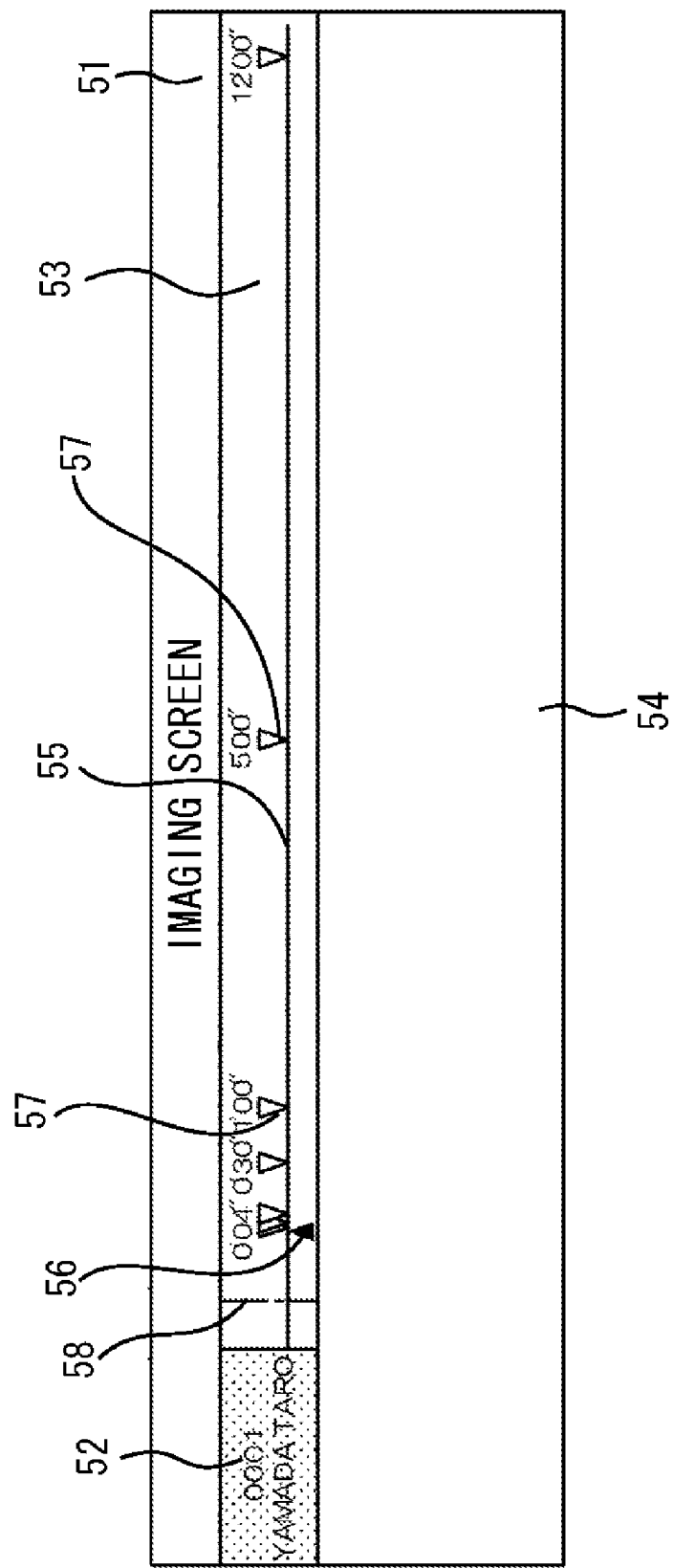
FIG. 10 illustrates an imaging screen just after fundus imaging is started.

When the selection of the examination start button 43 is detected, the display control unit 5 causes the display unit 15 to display an imaging screen 51 illustrated in FIG. 10. The imaging screen 51 includes an examination selection unit 52, an imaging sequence display unit 53, and an image display portion 54, which is a region for displaying a fundus image captured by the fundus camera 1.

Subject information and examination information stored in the appointed examination storage unit 10 are displayed on the examination selection unit 52. Therefore, the operator can easily grasp whose fundus is currently image-captured.

The examination selection unit 52 illustrated in FIG. 10 displays each subject's ID and name. However, displayed information is not limited to such subject information. The examination selection unit 52 can display a reception number or other information, which allows the operator to specify an examination.

The imaging sequence display unit 53 displays imaging sequences stored in the imaging sequence storage unit 7. The imaging sequences are displayed along a time axis 55. A fluorescence-agent intravenous-injection timing mark 56 indicating a timing of intravenous injection of a fluorescence agent, and a plurality of imaging timing marks 57 representing imaging timings are displayed along the time axis 55. A lapse time display line 58 representing a lapse time since the intravenous injection of a fluorescence agent is movably provided on the time axis 55.

The imaging screen 51 illustrated in FIG. 10 is a screen in a state in which fundus imaging is not performed on any subjects. Therefore, nothing is displayed on the image display portion 54.

Next, the operator makes the subject sit on a seat in front of the fundus camera 1. Then, the alignment adjustment and the focus adjustment of the subject's eye are performed. In addition, the operator intravenously injects a fluorescence agent into the subject. Then, the operator operates the timer start button of the examination instruction unit 11 simultaneously with the intravenous injection of the fluorescence agent.

When detecting the operation performed on the timer start button, the timer unit 6 starts measuring a lapse time. The display control unit 5 causes the lapse time display line 58 to move to the right along the time axis 55.

Upon completion of the above pre-imaging preparation, the operator pushes an imaging switch (not illustrated) to cause a flash unit to emit light. Then, imaging of a fundus of the subject's eye is performed. At this time, the operator performs imaging while checking a positional relationship between a displayed position of the lapse time display line 58 and each of positions of the imaging timing marks 57. Thus, the operator can perform fundus imaging according to the set imaging sequence.

Figure 11:
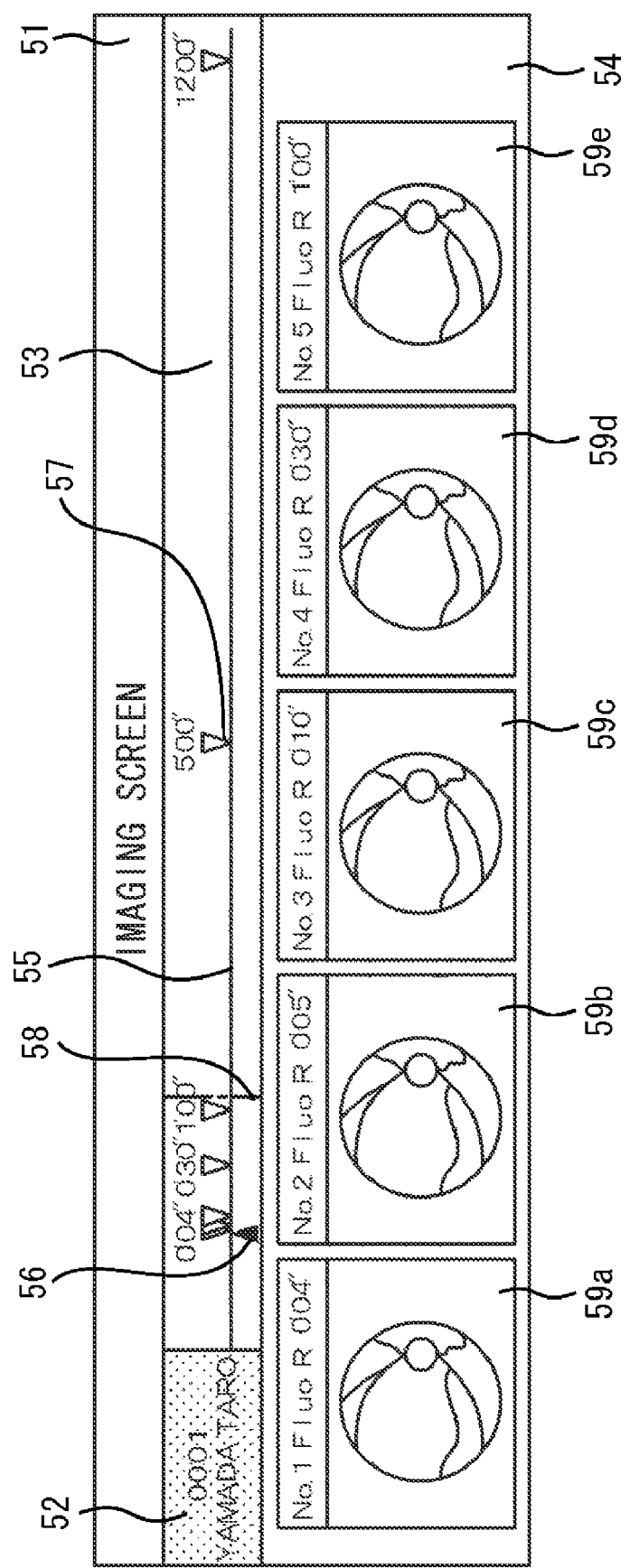
FIG. 11 illustrates an image captured 1 minute after fundus imaging is started.

FIG. 11 illustrates a state of the imaging screen 51 at 1 minute later since the intravenous injection of the fluorescence agent into the subject in the fundus imaging performed on the subject having ID "0001", who has been appointed an examination on the examination appointment screen 21 illustrated in FIG. 6. At that time, the operator has already performed fluorescence imaging of five fundus images according to the imaging sequence. The image display portion 54 displays captured five fundus images 59a through 59e.

Then, the operator observes the positions of the lapse time display line 58 on the imaging sequence display unit 53 and the next imaging timing mark 57. Thus, the operator can recognize that there is a waiting time of about four minutes until the next imaging timing. In order to improve examination efficiency, the operator can consider imaging of a fundus of another subject's eye during the waiting time.

Thus, when noticing presence of a large interval between adjacent imaging timings while performing imaging of a fundus of a subject's eye, sometimes, the operator desires to perform imaging of a fundus of another subject's eye during the large interval.

Figure 12:
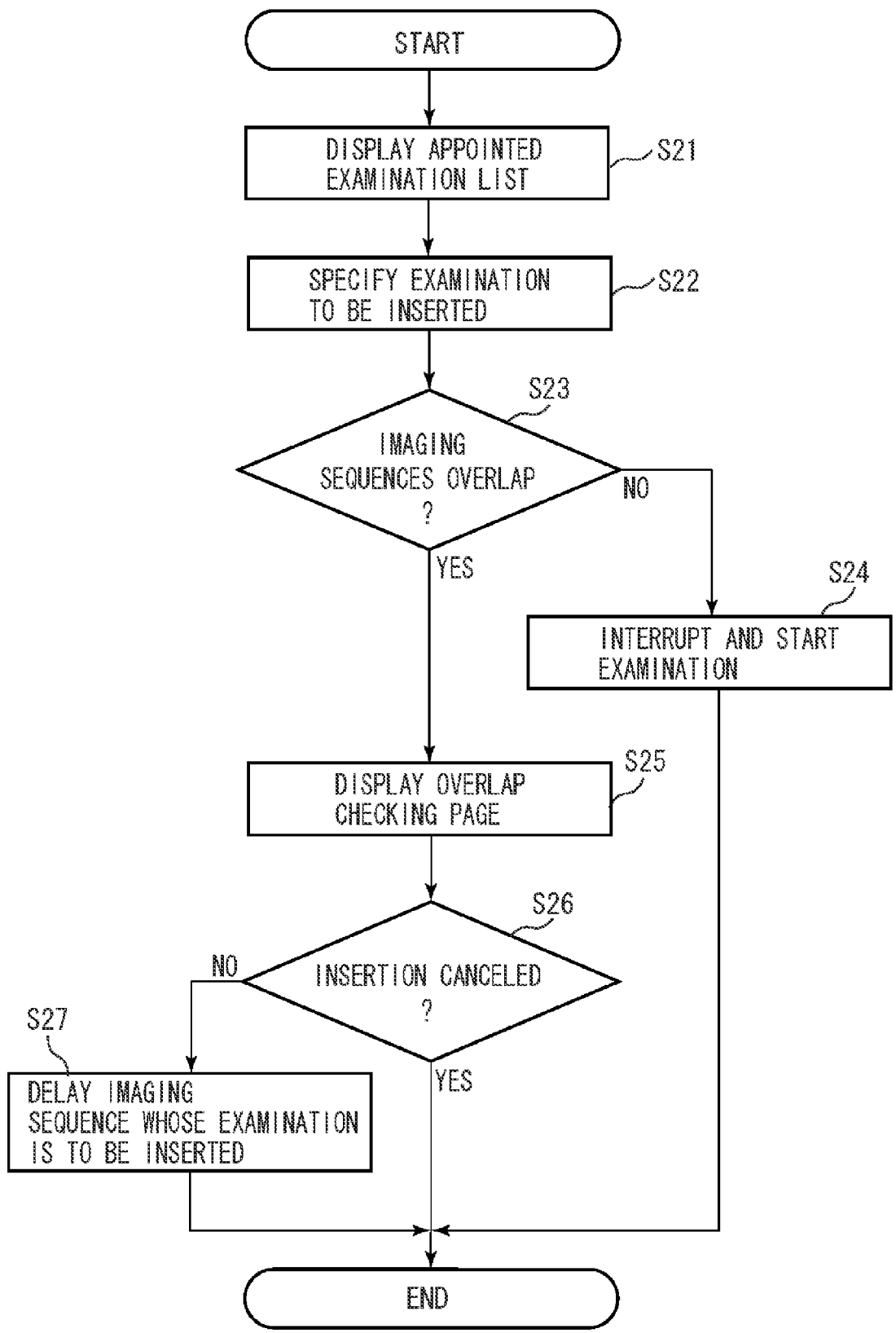
FIG. 12 is a flowchart illustrating a fundus imaging interrupt operation.

FIG. 12 is a flowchart illustrating an operation of performing the imaging of a fundus of another subject's eye while the imaging of the fundus of the current subject's eye is performed.

First, in step S21, when the examination instruction unit 11 detects an examination start operation performed by the operator, the display control unit 5 causes the display unit 15 to display the appointed examination list screen 41 illustrated in FIG. 9.

Next, in step S22, the examination instruction unit 11 selects a subject 42, whose examination seems to be able to finish in a relatively short time, in the appointed examination list screen 41.

When the examination start button 43 is operated by the operator, the examination instruction unit 11 detects that an examination to be inserted is specified. Here, an inserting operation is described by assuming that imaging of a fundus of a subject having ID "0002" is selected.

In step S22, the examination instruction unit 11 detects that the operator specifies an examination to be inserted. Then, in step S23, the overlapping determination unit 9 determines whether a imaging sequence corresponding to the currently performed imaging of the fundus temporally overlaps with that corresponding to the imaging of a fundus to be inserted.

If the overlapping determination unit 9 determines that these imaging sequences do not overlap each other (NO in step S23), the process proceeds to step S24. The overlapping determination unit 9 starts the inserted examination directly. On the other hand, if the overlapping determination unit 9 determines that these imaging sequences overlap each other (YES in step S23), the process proceeds to step S25, and the following steps are performed.

The operator can easily recognize that there is a waiting time of about four minutes until the next imaging is performed, as is seen on the imaging screen 51 illustrated in FIG. 11. Then, the operator is to start inserting of the imaging of an eye fundus of the subject having the ID of "0002" on the examination appointment screen 21 illustrated in FIG. 8.

A waiting time for the imaging of an eye fundus of the subject having the ID of "0001" is about four minutes. On the other hand, the imaging of a fundus of the subject having ID "0002" is an examination that can be finished in three minutes since the intravenous injection of the fluorescence agent. When the imaging of the eye fundus of the subject having ID "0002" is started immediately, the imaging sequences does not seem to overlap each other.

However, a pre-imaging preparation time and a post-imaging preparation time, illustrated in FIGS. 6 and 8, are set. Accordingly, when an operation of inserting the imaging of the eye fundus is performed, these preparation time periods should be taken into consideration. Particularly, the subject having ID of "0002" is at an advanced age. Accordingly, it should be considered that the preparation time periods for the subject having ID "0002" are long, as compared with those for a young subject.

Figure 13:
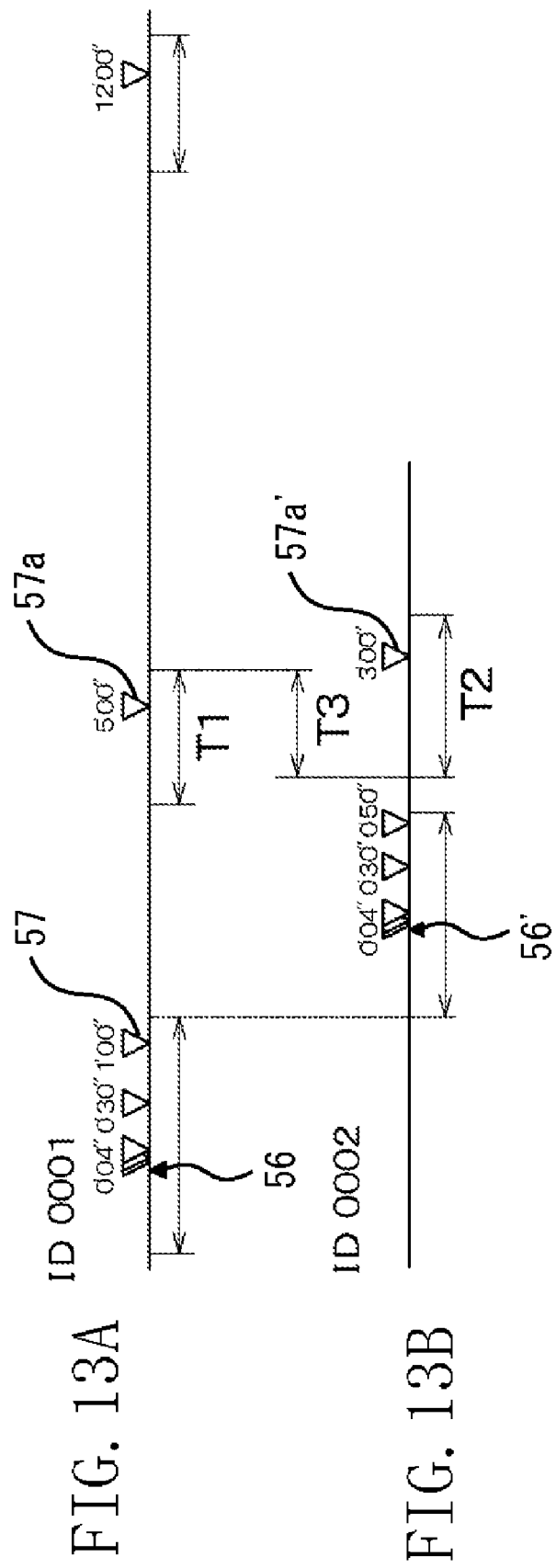
FIGS. 13A and 13B are timing charts each illustrating how imaging sequences overlap each other.

FIGS. 13A and 13B are flowcharts each illustrating how imaging sequences overlap each other when the insertion of the imaging of the eye fundus of the subject having ID "0002") into that of the subject having ID "0001", is started. FIG. 13A illustrates the imaging sequence of the subject having ID "0001". FIG. 13B illustrates the imaging sequence of the subject having ID "0002".

The imaging of the eye fundus of the subject having ID "0002" is inserted in the imaging of the eye fundus of the subject having ID "0001" at 1 minute later since the fluorescence agent is injected into the subject having ID "0001". A time period T1 is a preparation time for imaging a sixth image of the eye fundus of the subject having ID "0001", at an imaging timing 57a five minutes after the intravenous injection of a fluorescence agent that is performed at the fluorescence agent intravenous-injection timing 56 on the subject having ID "0001".

A time period T2 is a preparation time for imaging a sixth image of the eye fundus of the subject having ID "0002", at a imaging timing 57a' which is three minutes after the intravenous injection of a fluorescence agent, which is performed at the fluorescence agent intravenous-injection timing 56' to the subject having ID "0002".

The preparation time periods T1 and T2 overlap each other at about four minutes since the intravenous injection of the fluorescence agent into the subject having ID "0001". Thus, the imaging sequences thereof temporally overlap each other. If the imaging of the eye fundus of the subject having ID "0002" is inserted directly into the imaging of the eye fundus of the subject having ID "0001", the operator has no other choice but to give up performing the imaging of the eye fundus of one of the subject having ID "0001" and the subject having ID "0002".

Thus, the fundus imaging apparatus according to the present exemplary embodiment determines whether the imaging sequences, each of which includes the associated pre-imaging preparation time and the associated post-imaging preparation time, overlap each other.

Figure 14:
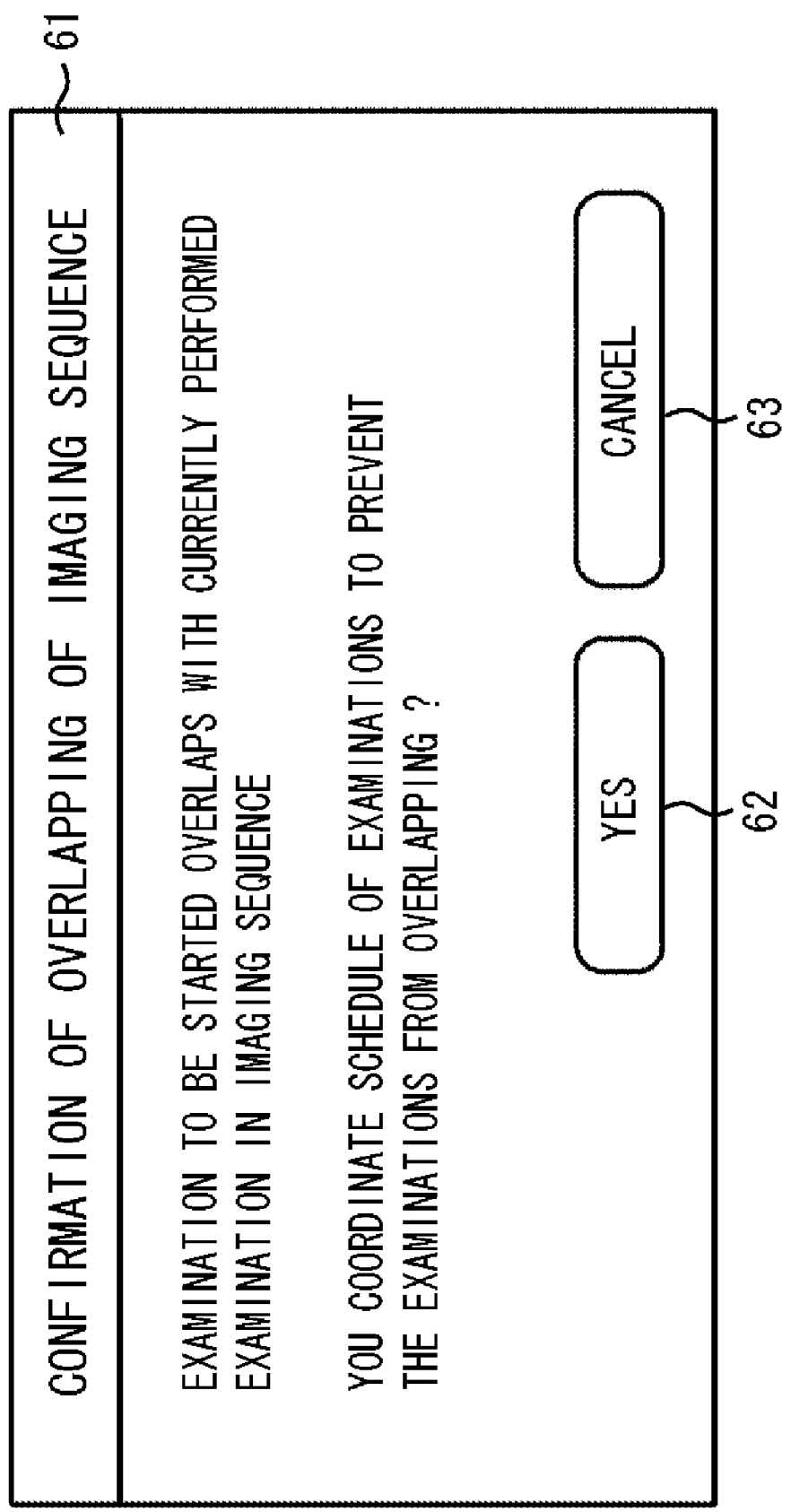
FIG. 14 illustrates an imaging sequence overlap confirmation screen.

In step S23, it is determined the imaging sequence for the fundus imaging to be inserted overlaps the imaging sequence for the currently performed fundus imaging (YES in step S23). Then, in step S25, the display control unit 5 causes the display unit 15 to display an overlap confirmation screen 61 for confirming the overlap between the imaging sequences illustrated in FIG. 14.

The overlap confirmation screen 61 is provided with a confirmation button 62 for starting an inserted examination, and a cancellation button 63 serving as an examination cancellation input unit for canceling the adjustment of inserting an examination. Accordingly, the operator can select one of an operation for starting insertion of an examination and an operation for canceling the insertion of an examination.

In step S26, if the selection of the cancellation button 63 is detected (YES in step S26), the insertion of an examination is canceled, so that the current examination is continued.

On the other hand, if the operator clicks the confirmation button 62 (NO in step S26), the process proceeds to step S27. In step S27, the imaging sequence adjustment unit 8 delays the imaging sequence of the imaging of the eye fundus to be inserted, and thus adjusts the imaging sequence.

Figure 15:
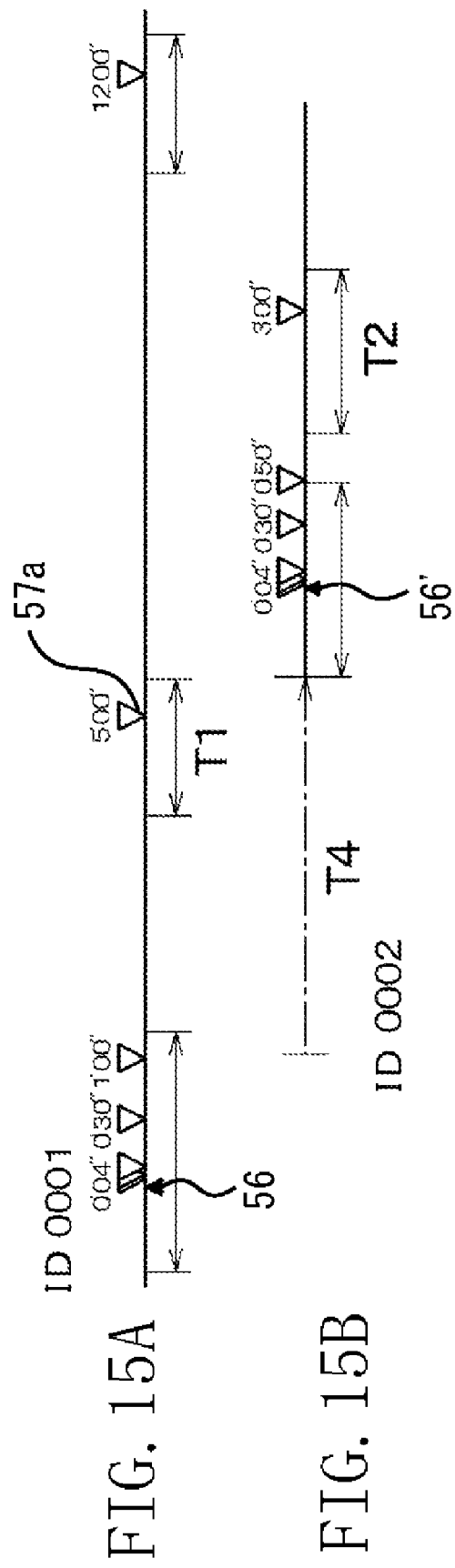
FIGS. 15A and 15B are charts illustrating imaging sequences respectively corresponding to different subjects.

For example, if the imaging sequences overlap each other as illustrated in the timing charts in FIGS. 13A and 13B, the imaging sequence adjustment unit 8 adjusts the imaging sequences as illustrated in FIGS. 15A and 15B. Similarly to FIGS. 13A and 13B, FIG. 15A illustrates an imaging sequence of the imaging of the eye fundus of the subject having ID "0001". FIG. 15B illustrates an imaging sequence of the imaging of the eye fundus of the subject having ID "0002".

The imaging sequence adjustment unit 8 delays the start of the imaging sequence of the subject having ID "0002", by a delay time T4. Thus, the imaging sequence adjustment unit 8 sets the start of the imaging sequence of the subject having ID "0002" after a sixth image of the fundus is taken at a timing indicated by the imaging timing mark 57a five minutes after the intravenous injection of the fluorescence agent into the subject having ID "0001".

Thus, the overlap between the preparation time T1 corresponding to the subject having ID "0001", and that of T2 corresponding to the subject having ID "0002", is eliminated. Accordingly, the imaging of the eye fundus of the subject having ID "0002", can safely be inserted.

FIGS. 15A and 15B illustrate an example including only one time zone into which the imaging operation of the imaging sequence of the subject having ID "0002", can be inserted. However, sometimes, there are a plurality of time zones into which the imaging operation according to the imaging sequence of the subject having ID "0002", can be inserted.

In this case, the imaging sequence adjustment unit 8 may specify a time zone into which an imaging operation is inserted so as to minimize the delay time T4. Thus, the imaging sequence adjustment unit 8 can determine the delay time T4.

According to the setting of the imaging sequence corresponding to the subject having ID "0001, there can be no time zone into which an imaging operation according to the imaging sequence for the subject having ID "0002" can be inserted.

In this case, the imaging sequence adjustment unit 8 adjusts the imaging sequence by delaying the imaging of the eye fundus of the subject having ID "0002", to a time at which the imaging sequence of the subject, having ID "0001" is completely finished.

In the above exemplary embodiment, it is assumed that fluorescence imaging is performed in an ophthalmologist's office. Thus, the above exemplary embodiment is constructed such that the entire imaging sequence is delayed without changing each of the imaging timings set in the imaging sequence.

This is because a fluorescence imaging method depends upon the lapse time since the intravenous injection of the fluorescence agent, so that the imaging timing cannot be changed. However, when a fundus of a subject's eye is image-captured using the color imaging, no fluorescence agent is used. Thus, importance for each imaging timing is not so high. Accordingly, another exemplary embodiment can be constructed to delay individual imaging timings instead of delaying the entire imaging sequence.

Figure 16:
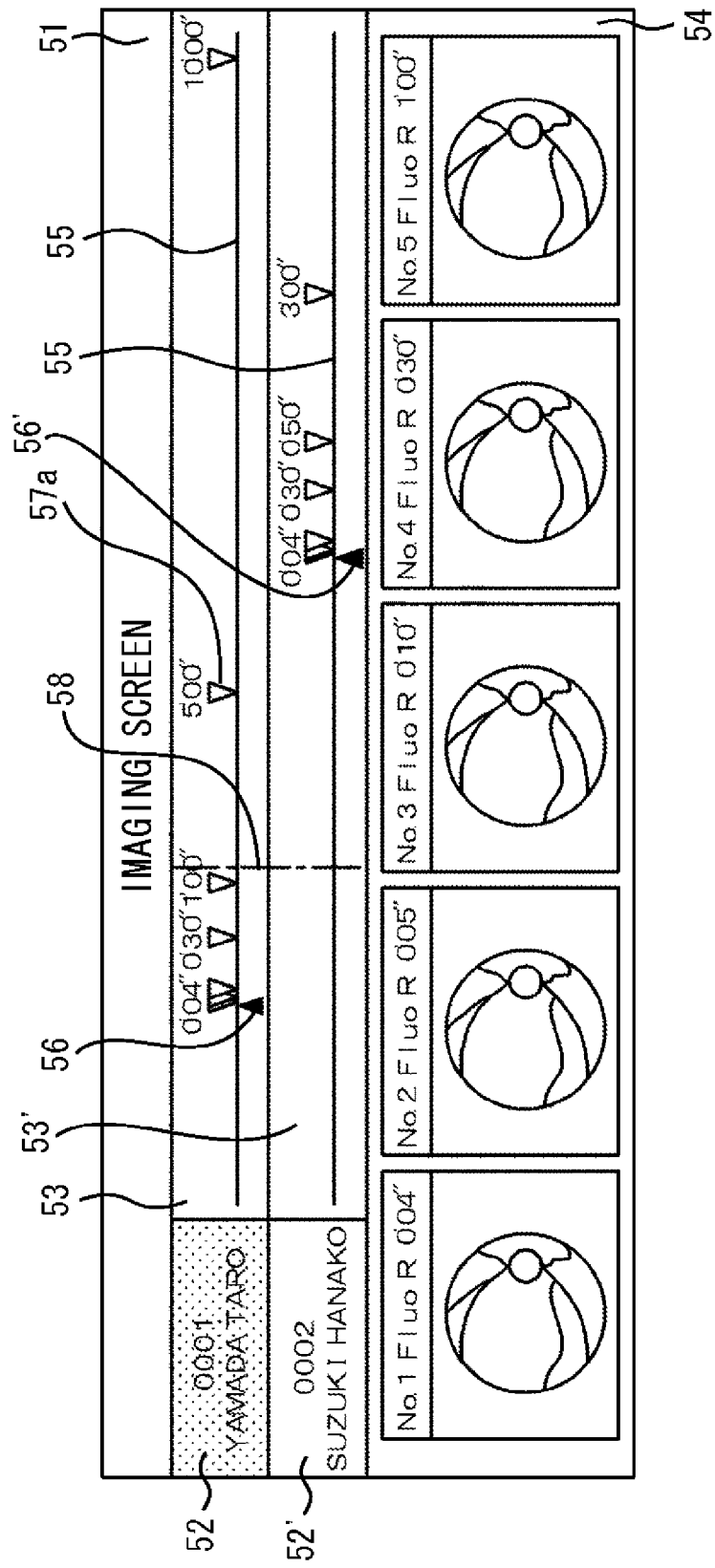
FIG. 16 illustrates an imaging screen when a fundus imaging operation is inserted while another fundus imaging operation is performed.

Next, in an operation after the imaging sequence corresponding to an inserted examination is delayed, the imaging screen 51 just after the imaging of an eye fundus of the subject having ID "0002", is inserted into the imaging of an eye fundus of the subject having ID "0001", is used, as illustrated in FIG. 16.

An examination selection portion 52' corresponding to the subject having ID "0002" is added to an examination selection portion 52 corresponding to the subject having ID "0001". Thus, it is clearly illustrated that two imaging operations are being performed. An imaging sequence display portion 53' corresponding to the subject having ID "0002" is added thereto.

The operator can change the subjects to be imaged by selecting the examination selection portion 52 or the examination selection portion 52'.

The imaging sequence for the subject having ID "0002" is delayed by the imaging sequence adjustment unit 8. Thus, the entire imaging sequence to be started at a moment corresponding to the fluorescence agent intravenous-injection timing mark 56' indicating the timing when the fluorescence agent is intravenously injected into the subject, is shifted to the right, as illustrated in FIG. 16.

Watching the adjusted imaging sequence, the operator can easily recognize that it is sufficient to start the imaging of the subject having ID "0002" after the imaging of a sixth image is finished at a moment corresponding to the imaging timing mark 57a indicating the timing of five minutes after the intravenous injection of a fluorescence agent.

When finishing the imaging of the sixth image of the subject having ID "0001" at the imaging timing mark 57a, the operator selects the examination selection portion 52' to start the imaging of the subject having ID "0002". Because the imaging sequence adjustment unit 8 assures a enough preparation time, the operator can easily perform an operation of having the subject with ID "0001" leave a seat, and an operation of preparing for imaging the subject having ID "0002".

In the present exemplary embodiment, an example has been described, in which the imaging of a fundus of a subject's eye is inserted while the imaging of a fundus of another subject's eye is being performed. However, the number of fundus imaging operations, into which another fundus imaging operation is inserted, is not limited to 1.

For example, as illustrated in FIG. 16, while two fundus imaging operations are performed, another fundus imaging operation can be inserted. In this case, the overlapping determination unit 9 determines whether an imaging sequence for a fundus imaging operation to be inserted overlaps each of the imaging sequences currently performed.

The fundus imaging apparatus according to the first exemplary embodiment includes an imaging sequence adjustment unit 8 for preventing, when a fundus imaging operation is inserted, imaging-sequences from overlapping. In addition, when an overlap between the imaging sequences is determined, a pre-imaging preparation time and a post-imaging preparation time are taken into consideration. Thus, an operator can safely insert an examination while sufficiently securing a time required to perform an operation for changing subjects to be imaged.

However, the delay time T4 is considerably increased depending on the imaging sequence to be inserted. Consequently, sometimes, a resultant state is substantially the same as that obtained by serially performing two fundus imaging operations.

In timing charts illustrated in FIGS. 15A and 15B, in a case where fluorescence imaging of a seventh image is added to an imaging sequence illustrated in FIG. 15B at five minutes after the timing of the fluorescence agent intravenous-injection timing mark 56', this additional fluorescence imaging operation cannot be inserted between the imaging of the sixth image and the seventh image in the imaging sequence illustrated in FIG. 15A. Therefore, the imaging sequence illustrated in FIG. 15B cannot be started until the imaging sequence illustrated in FIG. 15A is completely finished.

Figure 17:
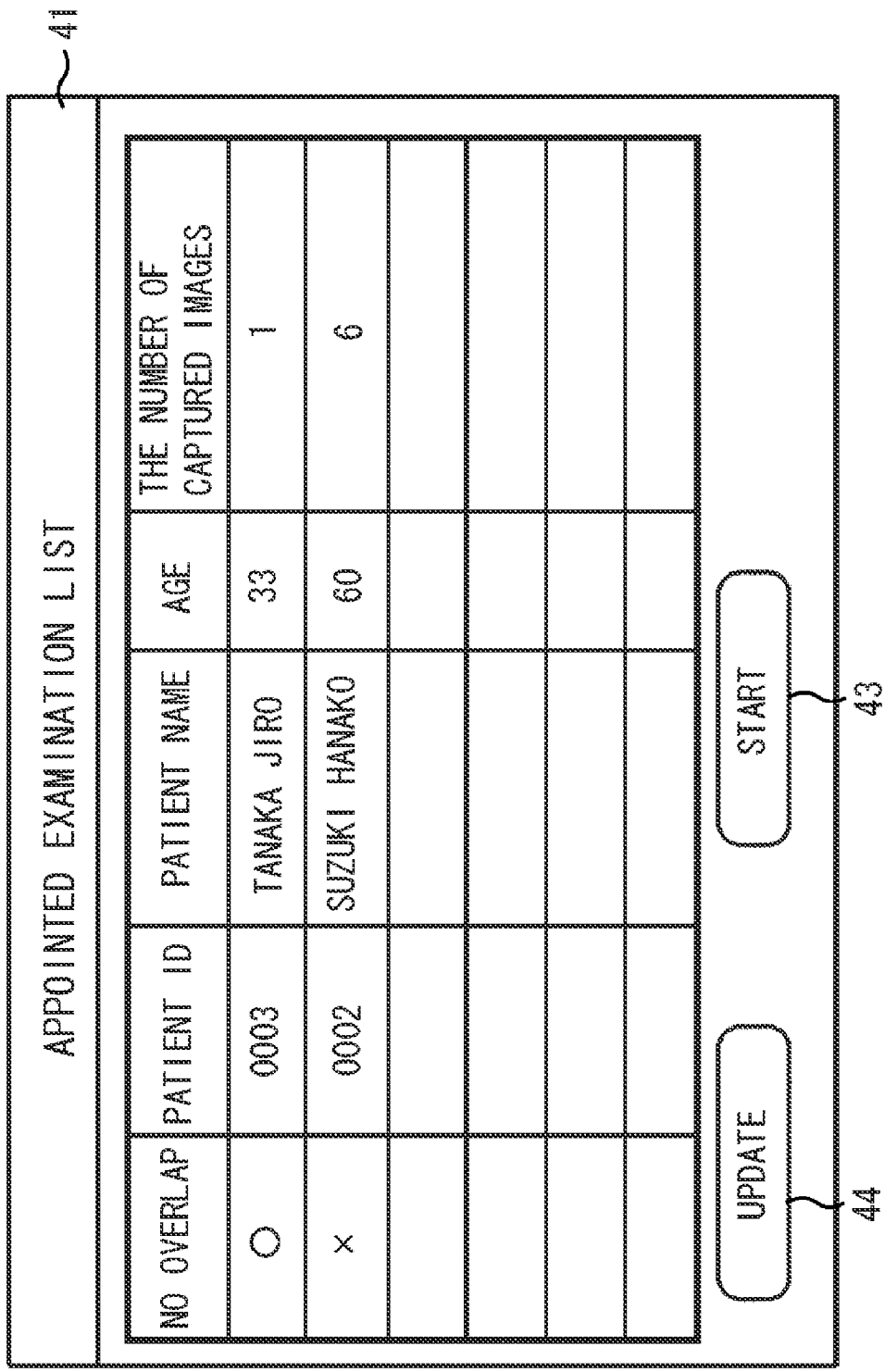
FIG. 17 illustrates an appointed examination list screen.

To this end, the fundus imaging apparatus according to the present exemplary embodiment can preliminarily display whether each appointed examination overlaps the currently performed sequence of fundus imaging operation, on the appointed examination list screen 41 illustrated in FIG. 17. Consequently, the operator can select and insert a fundus imaging operation of which the imaging sequence does not overlap the currently performed sequence of fundus imaging operation.

Figure 18:
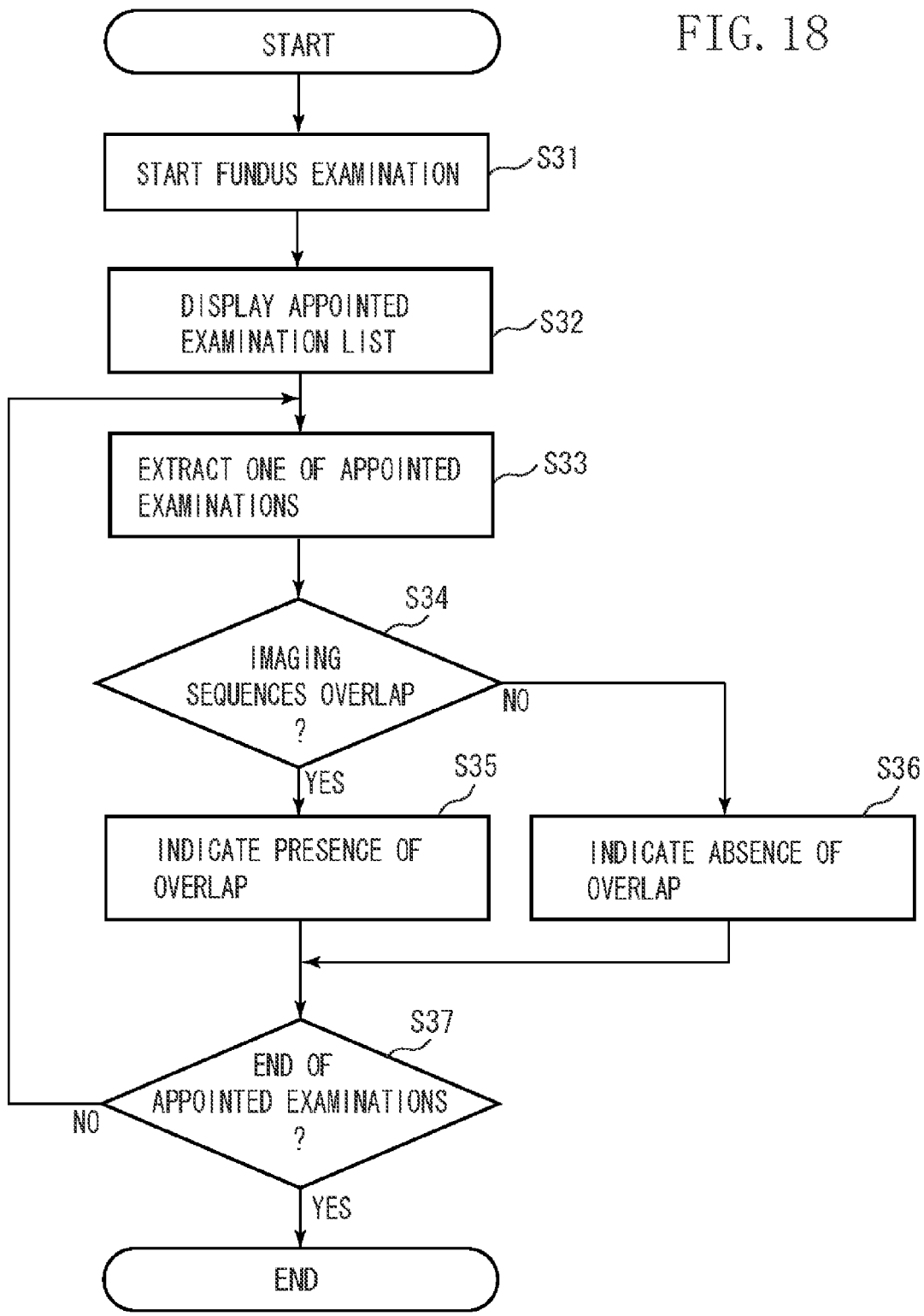
FIG. 18 is a flowchart illustrating a process for determining whether imaging sequences overlap each other.

FIG. 18 is a flowchart illustrating a process for determining whether the imaging sequences overlap each other.

First, in step S31, the operator starts imaging of a fundus of a certain subject's eye. At that time, elapsed time is measured by the timer unit 6 in response to the detection of an operation of the timer start button, as described above.

Then, in step S32, when an operation performed on the examination instruction unit 11 by the operator to insert imaging of a fundus of another subject's eye is detected at a stage when the fundus imaging has advanced to some extent, an appointed examination list screen 41 illustrated in FIG. 17 is displayed. On this appointed examination list screen 41, appointed examination information input via the examination appointment unit 12 is displayed on an appointed examination list line-by-line basis.

Next, in step S33, the overlapping determination unit 9 extracts subjects displayed on the appointed examination list screen 41 one by one. Then, in step S34, the overlapping determination unit 9 determines whether each imaging of a fundus of the extracted subject's eye overlaps the imaging sequence of currently performed imaging of a fundus if each of the imaging of the fundus of the extracted subject's eye is started at present.

When a plurality of fundus imaging operations are currently performed, when the imaging sequence of at least one of the plurality of currently performed fundus imaging operations overlaps the imaging of the fundus of the extracted subject's eye, the overlapping determination unit 9 determines that overlapping exist.

If the overlapping determination unit 9 determines that the imaging sequence of the extracted subject's eye overlaps the imaging sequence of the currently performed funds imaging operation (YES in step S34), in step S35, an "X" indicating the presence of overlapping is displayed on a line of the subject having ID "0002" in the appointed examination list. Then, the process proceeds to step S37.

On the other hand, if the overlapping determination unit 9 determines that the imaging sequence of the appointed examination does not overlap the imaging sequence of the currently performed fundus imaging operation (NO in step S34), a white circle "o" indicating the absence of an overlap is displayed on a line of the subject having ID "0003" in the appointed examination list. Then, the process proceeds to step S37.

Then, in step S37, it is determined whether the current appointed examination is the last one of the appointed examinations. Subsequently, the processing from step S33 through step S37 is repeated until overlapping determination on all of appointed fundus imaging operations is completed.

If the overlapping determination on all of appointed fundus imaging operations is completed (YES in step S37), the operator can easily distinguish an examination which does not overlap the imaging sequence of the currently performed examination, by means of the white circle "o" displayed on an associated line of the appointed examination list.

Thus, the operator can improve the examination efficiency by selecting the appointed examination from the appointed examination list screen 41 illustrated in FIG. 17, whose imaging sequence does not overlap the currently performed examination, and starting to insert the selected examination.

In the exemplary embodiment described above, overlapping determination processing beginning from step S33 is started when the appointed examination list screen 41 illustrated in FIG. 17 is displayed. However, a result of the overlapping determination on the imaging sequences changes with time.

For example, even when a certain imaging operation, which does not overlap the imaging sequence of the currently performed examination just after the appointed examination list screen 41 illustrated in FIG. 17 is displayed, this imaging operation may overlap the imaging sequence of currently performed examination one minutes after.

Therefore, an update button 44 is provided on the appointed examination list screen 41 illustrated in FIG. 17. When an operation performed on the update button 44 by the operator is detected, the overlapping determination processing beginning from step S33 is also started. Thereby, the operator can check overlapping states of the imaging sequences again according to the selection of the update button 44 before an examination to be inserted is selected.

Alternatively, the apparatus can be constructed such that the overlapping determination processing performed from step S33 is started without operating the update button 44. In this case, the operator can check the latest overlapping state of the imaging sequences without performing a specific operation.

According to another example, the apparatus can be constructed such that only examinations which do not overlap the currently performed sequence of fundus imaging operation may be selectively displayed on the appointed examination list screen 41 as illustrated in FIG. 9. At that time, because all of the appointed examinations displayed thereon do not overlap the imaging sequence of the currently performed fundus imaging operation, the operator can insert the appointed examination therebetween without bothering about the overlap.

Figure 19:
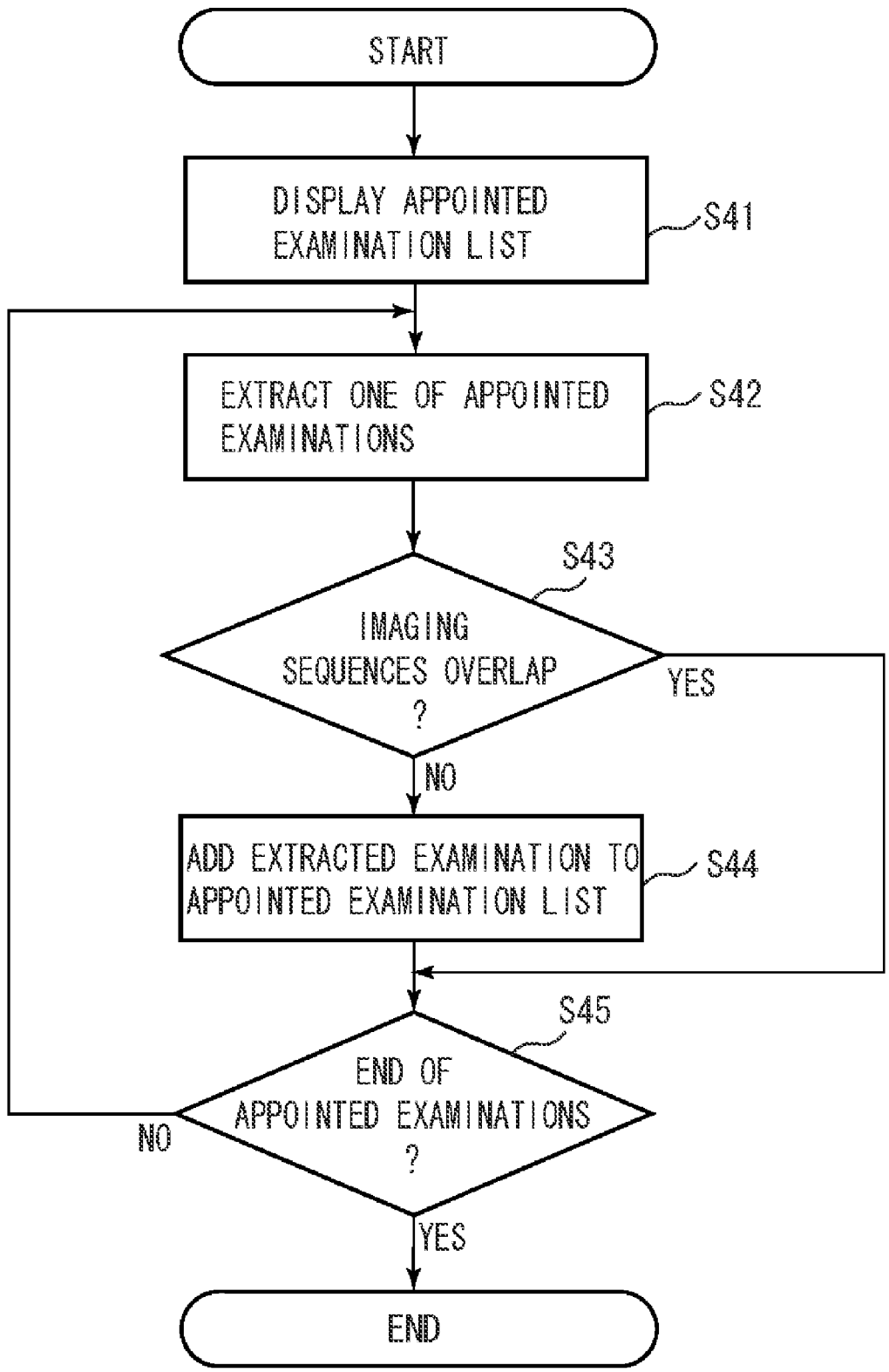
FIG. 19 is a flowchart illustrating another process for determining whether imaging sequences overlap each other.

FIG. 19 is a flowchart of the above processing. First, in step S41, in order to insert a fundus imaging operation, the examination instruction unit 11 detects a start operation performed by the operator. Then, the display control unit 5 causes the display unit 15 to display the appointed examination list screen 41 illustrated in FIG. 9. An appointed examination to be displayed on the appointed examination list screen 41 is determined in steps that will be described below. At this point of time, the appointed examination list screen 41 is displayed in a state in which no appointed examination is present.

Next, in step S42, the overlapping determination unit 9 extracts examinations displayed on the appointed examination list one by one. Then, in step S43, the overlapping determination unit 9 determines whether the imaging of a fundus of the extracted subject's eye overlaps the imaging sequence of a currently performed imaging of a fundus when the imaging of the fundus of the extracted subject's eye is started at present.

If a plurality of fundus imaging operations are currently performed, when the imaging sequence of at least one of the plurality of currently performed fundus imaging operations overlaps the imaging of the fundus of the extracted subject's eye, the overlapping determination unit 9 determines that there is an overlap (YES in step S43). If the overlapping determination unit 9 determines that there is no overlap (NO in step S43), in step S44, the extracted examination is added to the appointed examination list.

On the other hand, if the overlapping determination unit 9 determines that the imaging sequence of the extracted examination overlaps the imaging sequence of the currently performed imaging operation (YES in step S43), the extracted examination is not displayed on the appointed examination list. Then, the process proceeds to step S45.

Then, in step S45, it is determined whether the current appointed examination is the last one of the appointed examinations. If it is determined that the current appointed examination is the last one of the appointed examinations (YES in step S45), the process is finished. If it is determined that the current appointed examination is not the last one of the appointed examinations (NO in step S45), the processing from step S42 through step S45 is repeated until overlapping determination on all of the appointed fundus imaging operations is completed.

Then, if the overlapping determination on all of the appointed fundus imaging operations is completed (YES in step S45), only appointed examinations, which does not overlap the sequence of the currently performed fundus imaging operation, are displayed on the appointed examination list screen 41 as illustrated in FIG. 9.

The operator can improve the examination efficiency by selecting arbitrarily the appointed examination from the appointed examination list screen 41, and starting to insert the selected examination.

Figure 20:
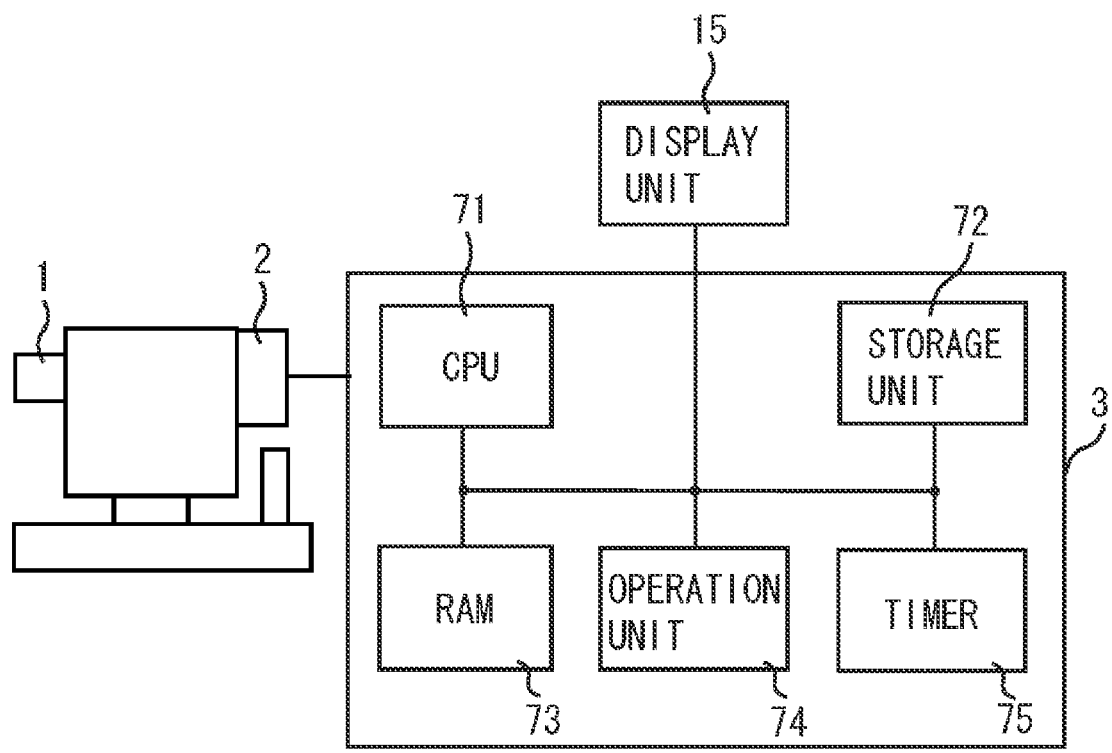
FIG. 20 schematically illustrates a hardware configuration of an information processing apparatus.

FIG. 20 schematically illustrates a configuration of hardware of the information processing apparatus 3. A central processing unit (CPU) 71 is a control unit for performing overall control of the entire information processing unit 3. The CPU 71 corresponds to the display control unit 5, the imaging sequence adjustment unit 8, the overlapping determination unit 9, the imaging sequence registration unit 13, and the preparation time setting unit 14, which are illustrated in FIG. 1.

A storage unit 72 (e.g., hard disk drive) stores programs which can be executed by a computer for performing overall control of the entire information processing apparatus 3. The storage unit 72 stores also images captured by the digital camera 2, and the registered imaging sequences.

The storage unit 72 corresponds to the image storage unit 4, the imaging sequence storage unit 7, the appointed examination storage unit 10, and the storage portion, which stores the table, in the preparation time setting unit 14. A random access memory (RAM) 73 is a memory for temporarily storing programs and the like read from the storage unit 72. An operation unit 74 includes a mouse, a keyboard, a touch panel, and the like and corresponds to the examination instruction unit 11 and the examination appointment unit 12. A timer 75 corresponds to the timer unit 6.

In the exemplary embodiments, a fundus imaging apparatus has been described. However, the present invention can be applied to a medical imaging apparatus for medical examinations, such as an X-ray imaging apparatus.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2008-167062 filed Jun. 26, 2008, which is hereby incorporated by reference herein in its entirety.

What is claimed is:

1. An apparatus comprising:
   an overlapping determination unit configured to determine an overlapping between a first preparation time for preparing an imaging of a subject that is currently performed and a second preparation time for preparing an imaging of a subject that is to be started; and
   an adjusting unit configured to delay the second preparation time to a time at which the second preparation time does not overlap the first preparation time.

2. The apparatus according to claim 1, further comprising:
   a cancellation input unit configured to cancel starting of the imaging that is to be started,
   wherein the cancellation input unit includes an operation selection unit capable of selecting, based on a result of determination made by the overlapping determination unit, the adjustment of the second preparation time by the adjusting unit or cancellation of starting the imaging.

3. The apparatus according to claim 1, further comprising a preparation time setting unit configured to set the second preparation time as a pre-imaging preparation time and the first preparation time as a post-imaging preparation time, which are respectively needed before and after the imaging.

4. The apparatus according to claim 1, further comprising a determination unit configured to determine the first and second preparation time according to at least one of an imaging mode and a subject's age.

5. The apparatus according to claim 1, further comprising an overlap display unit configured to display appointment information as a list, based on a result of determination made by the overlapping determination unit.

6. The apparatus according to claim 5, wherein the overlap display unit displays the result made by the overlapping determination unit together with the appointment information.

7. The apparatus according to claim 5, wherein the overlap display unit selectively displays the appointment information of the second preparation time not to overlap the first preparation time.

8. A method comprising:
   determining an overlapping between a first preparation time for preparing an imaging of a subject that is currently performed and a second preparation time for preparing an imaging of a subject that is to be started; and
   delaying the second preparation time to a time at which the second preparation time does not overlap the first preparation time.

9. A non-transitory computer readable storage medium storing a computer-executable program of instructions for causing a computer to perform a method, the method comprising:
   determining an overlapping between a first preparation time for preparing an image of a subject that is currently performed and a second preparation time for preparing an image of a subject that is to be started; and
   delaying the second preparation time to a time at which the second preparation time does not overlap the first preparation time.

10. The method according to claim 8, further comprising displaying appointment information as a list based on a result of the determination.

11. The apparatus according to claim 1, wherein the imaging is a fluorescence imaging of a subject's eye of the subject, and further comprising a determination unit configured to determine a plurality of fluorescence imaging timings according to an elapsed time of the fluorescence imaging.

12. An apparatus comprising:
   an overlapping determination unit configured to determine an overlapping between a first preparation time for preparing an examination that is currently performed and a second preparation time for preparing an examination that is to be started; and
   an adjusting unit configured to delay the second preparation time to a time at which the second preparation time does not overlap the first preparation time.

13. An apparatus comprising:
   an imaging interval setting unit configured to set an imaging interval of a first examination for imaging a subject's eye of a first subject a plurality of times and an imaging interval of a second examination for imaging a subject' eye of a second subject a plurality of times; and
   an adjusting unit configured to adjust, based on the set imaging interval of the first examination and the set imaging interval of the second examination, an imaging timing such that at least one of the plurality of imagings of the second examination is performed between the plurality of imagings of the first examination.

14. The apparatus according to claim 13, further comprising a display control unit configured to control a display unit to display the display configuration which indicates the adjusted imaging timing.

15. A method comprising:
   setting an imaging interval of a first examination for imaging a subject's eye of a first subject a plurality of times and an imaging interval of a second examination for imaging a subject's eye of a second subject a plurality of times; and
   adjusting, based on the set imaging interval of the first examination and the set imaging interval of the second examination, an imaging timing such that at least one of the plurality of imagings of the second examination is performed between the plurality of imagings of the first examination.

16. A non-transitory computer readable storage medium storing a computer-executable program of instructions for causing a computer to perform a method for performing a plurality of examinations of each of a plurality of subjects, the method comprising:

setting an imaging interval of a first examination for imaging a subject's eye of a first subject a plurality of times and an imaging interval of a second examination for imaging a subject's eye of a second subject a plurality of times; and adjusting, based on the set imaging interval of the first examination and the set imaging interval of the second examination, an imaging timing such that at least one of the plurality of imagings of the second examination is performed between the plurality of imagings of the first examination.

17. An apparatus, comprising:

first determination unit configured to determine a first a plurality of imaging timings for acquiring fluorescence images of a subject's eye according to an elapsed time of a fluorescence imaging of a subject's eye; and a second determination unit configured to determine a second imaging timing for acquiring an image of a subject's eye based on an imaging interval of the first plurality of imaging timings.

18. The apparatus according to claim 17, further comprising an overlapping determination unit configured to determine an overlapping between a first preparation time of the first plurality of imaging timings that is currently performed and a second preparation time of a second imaging timing that is to be started.

19. The apparatus according to claim 18, further comprising an adjusting unit configured to delay the second preparation time to a time at which the second preparation time does not overlap the first preparation time.

20. The apparatus according to claim 19, further comprising a display control unit configured to control a display unit to display the display configuration which indicates the imaging interval.

21. The apparatus according to claim 18, further comprising a display control unit configured to control a display unit to display the display configuration which indicates the second preparation time.

22. The apparatus according to claim 1, further comprising a display control unit configured to control a display unit to display the display configuration which indicates the delayed second preparation time.

23. The apparatus according to claim 17, further comprising a display control unit configured to control a display unit to display the display configuration which indicates first plurality of imaging timings, the display configuration which indicates the second imaging timing, the display configuration which indicates an elapsed time and the fluorescence images.

24. An apparatus comprising:

an overlapping determination unit configured to determine an overlapping between a first preparation time for preparing an imaging of a subject that is currently performed and a second preparation time for preparing an imaging of a subject that is to be started; and a preparation time setting unit configured to set the second preparation time as a pre-imaging preparation time and the first preparation time as a post-imaging preparation time, which are respectively needed before and after the imaging.

25. An apparatus comprising:

a first determination unit configured to determine a first plurality of imaging timings for acquiring images of a subject and a second plurality of imaging timings for acquiring images of a subject; and a second determination unit configured to determine an imaging interval of the first and second pluralities of imaging timings according to at least one of an imaging mode and a subject's age.

26. The apparatus according to claim 12, wherein the examination is a fluorescence imaging of a subject's eye, and further comprising a determination unit configured to determine a plurality of fluorescence imaging timings according to an elapsed time of the fluorescence imaging.

27. The apparatus according to claim 12, further comprising an imaging timing setting unit configured to set a plurality of imaging timings of each of the examinations.

28. The apparatus according to claim 1, further comprising an imaging timing setting unit configured to set a plurality of imaging timings of each of the subjects.

* * * * *